United States Patent
Maier et al.

(10) Patent No.: US 7,256,875 B2
(45) Date of Patent: Aug. 14, 2007

(54) METHOD FOR DETECTION OF PATHOGENIC MICROORGANISMS

(75) Inventors: John S. Maier, Pittsburgh, PA (US); Charles W. Gardner, Jr., Gibsonia, PA (US); Matthew P. Nelson, Harrison City, PA (US); Robert C. Schweitzer, Pittsburgh, PA (US); Patrick J. Treado, Pittsburgh, PA (US); G. Steven Vanni, Alexandria, VA (US); Julianne Wolfe, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

(21) Appl. No.: 11/440,845

(22) Filed: May 25, 2006

(65) Prior Publication Data

US 2007/0086003 A1 Apr. 19, 2007

Related U.S. Application Data

(63) Continuation-in-part of application No. 11/079,493, filed on Mar. 14, 2005, now Pat. No. 7,113,275, which is a continuation of application No. 10/823,902, filed on Apr. 14, 2004, now Pat. No. 6,917,423, which is a continuation of application No. 10/339,807, filed on Jan. 10, 2003, now Pat. No. 6,765,668.

(60) Provisional application No. 60/347,806, filed on Jan. 10, 2002.

(51) Int. Cl.
*G01J 3/44* (2006.01)
*G01N 21/65* (2006.01)

(52) U.S. Cl. .................. 356/72; 356/301; 250/339.05; 250/339.12

(58) Field of Classification Search .................. 356/72, 356/301

See application file for complete search history.

(56) References Cited

U.S. PATENT DOCUMENTS

| | | | |
|---|---|---|---|
| 4,880,052 A | 11/1989 | Meyer, IV et al. | |
| 5,194,912 A | 3/1993 | Batchelder et al. | |
| 5,377,004 A | 12/1994 | Owen et al. | |
| 5,442,438 A | 8/1995 | Batchelder et al. | |
| 5,528,393 A | 6/1996 | Sharp et al. | |
| 5,539,517 A | 7/1996 | Cabib et al. | |
| 5,623,342 A | 4/1997 | Baldwin et al. | |
| 5,689,333 A | 11/1997 | Batchelder et al. | |

(Continued)

FOREIGN PATENT DOCUMENTS

JP 9-121889 A 5/1997

OTHER PUBLICATIONS

Caetano et al., "Evaluation of the Importance of Non-Linear Spectral Mixing in Coniferous Forests," SPIE vol. 3499, Sep. 1998, pp. 257-269.

(Continued)

*Primary Examiner*—F. L. Evans
(74) *Attorney, Agent, or Firm*—Morgan, Lewis & Bockius LLP

(57) ABSTRACT

A method for the detection and identification of pathogenic microorganisms using Raman scattered light and transmitted light in the near infrared spectral region. The method may include passing the Raman scattered light and transmitted light through a FAST fiber array spectral translator.

24 Claims, 37 Drawing Sheets

U.S. PATENT DOCUMENTS

| | | | |
|---|---|---|---|
| 5,710,626 A | | 1/1998 | O'Rourke et al. |
| 5,841,139 A | * | 11/1998 | Sostek et al. .......... 250/339.12 |
| 5,862,273 A | | 1/1999 | Pelletier |
| 5,866,430 A | | 2/1999 | Grow |
| 5,901,261 A | | 5/1999 | Wach |
| 5,911,017 A | | 6/1999 | Wach et al. |
| 6,002,476 A | | 12/1999 | Treado |
| RE36,529 E | | 1/2000 | Lewis et al. |
| 6,717,668 B2 | | 4/2004 | Treado et al. |
| 6,734,962 B2 | | 5/2004 | Treado et al. |
| 6,765,668 B2 | | 7/2004 | Gardner et al. |
| 6,917,423 B2 | | 7/2005 | Gardner et al. |
| 6,954,667 B2 | | 10/2005 | Treado et al. |
| 6,965,793 B2 | | 11/2005 | Treado et al. |

OTHER PUBLICATIONS

Rasmussen et al., "Library Retrieval of Infrared Spectra Based on Detailed Intensity Information," Applied Spectroscopy, vol. 33, No. 4, 1979, pp. 371-376.

Guilment et al., "Infrared Chemical Micro-Imaging Assisted by Interactive Self-Modeling Multivariate Analysis," Applied Spectroscopy, vol. 48, No. 3, 1994, pp. 320-326.

Malinowski, Edmund R., "Factor Analysis in Chemistry," 1991, 2nd Edition, Published by John Wiley & Sons, Inc./William H. Press et al.

Remote Sensing for Agriculture, Ecosystems, and Hydrology; Sep. 22-24, 1998; SPIE vol. 3499.

Numerical Recipes in C, The Art of Scientific Computing; Second Edition; originally published 1992—latest publication date 2002; published by Press Syndicate of the University of Cambridge.

* cited by examiner

METHOD FOR DETECTION OF PATHOGENIC MICROORGANISMS

CROSS REFERENCE TO RELATED APPLICATIONS

This application is a continuation-in-part of U.S. application Ser. No. 11/079,493 filed Mar. 14, 2005 now U.S. Pat. No. 7,113,275, which is a continuation of U.S. patent application Ser. No. 10/823,902, filed Apr. 14, 2004, now U.S. Pat. No. 6,917,423, which is a continuation of U.S. patent application Ser. No. 10/339,807, filed Jan. 10, 2003, now U.S. Pat. No. 6,765,668 which claims priority to U.S. patent application Ser. No. 60/347,806, filed Jan. 10, 2002.

FIELD OF THE INVENTION

The present invention relates to the field of chemical and biological analysis and more specifically to the use of Raman and near-infrared imaging spectroscopy to quickly identify chemical and biological agents.

BACKGROUND OF THE INVENTION

Terrorist deployment of chemical and/or infectious biological agents as weapons of mass destruction threatens the welfare of the human populace. Public concern has grown, especially in our nation, as terrorist uses of biothreat agents, such as Anthrax, become reality. Nightmare images of tens of thousands of infected and dying innocent victims strike fear in the hearts of nearly everyone. Biological and chemical warfare is significant, not only in lives lost, but also in the cost to the US economy. The Centers for Disease Control estimates that the loss of 100,000 lives will have a $29 B economic impact. The mass destruction potential of Biological Warfare Agents ("BWAs") and Chemical Warfare Agents (CWAs) is thought by many to be comparable to or even greater than that of nuclear weapons. Nuclear weapons have the potential to affect a finite area, albeit very large, and the use of such weapons is immediately obvious after the fact. BWAs and CWAs, on the other hand, have virtually no boundaries and have the potential to spread silently and unchecked through populations far from ground zero. Likewise, technology to rapidly detect and quantify very low levels of radioactive contamination is widely available. Unfortunately, such technology for BWAs and CWAs at similar levels is not definitive, not widely available and in many cases, is not very rapid.

The psychological impact of this type of threat is also very significant. The public is becoming increasingly aware of new, emerging pathogens. Fears over the unseen nature of BWAs and CWAs make for a very effective terrorism weapon in and of itself. In addition to perception, there is a very real threat due to incredible advances in biotechnology. It is now possible to alter the most virulent bacterium or virus and to increase both its pathogenicity and resistance to conventional therapy. The molecular biology revolution has now been underway for more than three decades, and the sheer number of persons with technical expertise to potentially create such weapons of mass destruction has consequently increased. In this age of advanced global travel, the likelihood of rapid dissemination of any type of BWA worldwide in a very short period of time is high, and the general public is well aware of this fact.

Conventional means of identifying pathogens using biology tools such as specific antibodies, genetic markers or propagation in culture are fundamentally slow and require hands-on manipulations. Furthermore, as new BWAs and CWAs are engineered, these conventional tools are likely to become less and less effective. As the use of BWAs and CWAs by terrorists becomes a reality, there is an increasing need to develop tools that can rapidly and accurately detect and classify these agents at a molecular level without coming into contact with them. These tools are needed to help expand our understanding of the biological and chemical basis of such warfare agents and the potential impact on the human body. Furthermore, the knowledge gained through such molecular analyses helps identify new targets for therapeutic and preventative agents.

SUMMARY OF THE INVENTION

A spectroscopic imaging system, also described as a chemical imaging system, employing Raman, fluorescence, UV-visible reflectance/absorption and/or near-infrared (NIR) reflectance/absorption spectroscopic techniques for characterization of BWAs and CWAs is disclosed.

In one embodiment, Raman microscopic imaging spectroscopy and/or fluorescence microscopic imaging spectroscopy can be used to detect, classify, identify and/or visualize BWAs, CWAs and non-threatening compounds. Microscopic imaging spectroscopy detects, classifies and identifies sub-micron size particles, including single bacterium. In addition, Raman microscopic imaging spectroscopy can perform sub-micron size particle detection, classification, identification and visualization of BWAs and CWAs in the presence of non-threatening 'masking' compounds when appropriate data analysis techniques are applied.

In another embodiment, Raman microscopic imaging spectroscopy in combination with near infrared microscopic imaging spectroscopy can be used to detect, classify, identify and/or visualize BWAs, CWAs and non-threatening compounds. Microscopic imaging spectroscopy detects, classifies and identifies sub-micron size particles. In addition, Raman microscopic imaging combined with near infrared microscopic imaging spectroscopy can perform sub-micron size particle detection, classification, identification and visualization of BWAs and CWAs in the presence of non-threatening 'masking' compounds when appropriate data analysis techniques are applied.

In another embodiment, fluorescence and Raman macroscopic imaging spectroscopy can be used to detect, classify, identify and/or -visualize BWAs, CWAs and non-threatening compounds. These macroscopic imaging techniques can perform sub-millimeter size particle detection, classification, identification and visualization of BWAs and CWAs (i.e., agglomerated bacteria and endospore detection and identification). In addition, fluorescence and Raman macroscopic imaging spectroscopy can perform detection, classification, identification and visualization of BWAs and CWAs in the presence of non-threatening 'masking' compounds when appropriate data analysis techniques are applied.

In another embodiment, Raman fiber optic dispersive spectroscopy can detect, classify and/or identify BWAs, CWAs and non-threatening compounds. Moreover, Raman fiber optic imaging spectroscopy can detect, classify, identify and/or visualize BWAs, CWAs and non-threatening compounds when appropriate data analysis techniques are applied.

In order to provide faster real-time analysis, Fiber-Array Spectral Translator (FAST) dispersive spectroscopy is used for rapid detection, classification and identification of BWAs, CWAs and non-threatening compounds. In addition, Fiber-Array Spectral Translator (FAST) imaging spectroscopy can be used for rapid detection, classification, identification and visualization of BWAs, CWAs and non-threatening compounds when appropriate data analysis techniques are applied.

The systems described above are applied in a variety of modes. The system is applied as a laboratory or transportable field Raman microscope such as ChemImage's FALCON Raman microscope outfitted with ChemImage's Simultaneous Imaging and Spectroscopy Apparatus. The system is also applied as a UV/Vis/NIR fluorescence, Raman, or UV/Vis/NIR/Mid-IR absorption/reflectance macroscope system such as ChemImage's CONDOR Macroscope. Alternatively, the system is applied as a laboratory or field fiberscope such as ChemImage's RAVEN endoscope. In addition, the system is applied as a laboratory or field Fiber-Array Spectral Translator (FAST) probe. Each of the modes of application are used separately or in combination with one another to achieve the desired speed and results.

Spectroscopic imaging techniques are applied to sensors designed to detect, classify, identify and/or visualize BWAs, CWAs and non-threatening compounds in ambient air. A schematic of such a sensor is shown in FIG. 1. The vacuum created by an air-sampling pump pulls the ambient air through the sample inlet and through the filter. Filter materials could include porous polypropylene or cellulose, in disk or roll form. Particulates in the air sample are trapped on the surface of the filter medium and are held in the field of view of the spectroscopic imaging system. The source, chosen specifically for the type of molecular spectroscopy being used, illuminates the trapped particles and induces either Raman or fluorescence emission from the sample. The imaging detector measures the spatial distribution of emitted light at a series of wavelengths and creates the data file used for further analysis. The inlet to this imaging detector can either be an imaging optical fiber or conventional optics. Advanced chemometric techniques along with image analysis routines are used to detect, classify, identify and/or visualize BWAs, CWAs and non-threatening compounds.

The system can be automated through the use of robotics or combined macro/micro instrumentation in order to target BWAs, CWAs and non-threatening agents. Using laser ablation and/or chemical ablation, the system can be automated to eradicate BWAs and CWAs post-targeting.

A variety of data processing procedures can be used with the system. A weighted spectral image data subtraction routine can be used to suppress contribution from microscope slide. Alternatively, multivariate image analysis involving principal factor analysis and subsequent factor rotation can be used for differentiation of pure molecular features in BWAs, CWAs and non-threatening 'masking' compounds.

BRIEF DESCRIPTION OF THE DRAWINGS

FIGS. 5I-5N (Sample 1291-006) show Raman, IR and SEM-EDS results on the remaining unidentified powders. There are 3 distinct types of powders in this sample. All 3 have organic content, while 2 of the 3 are fairly rich in aluminosilicates. One of the powders is likely a complex aromatic hydrocarbon.

FIGS. 5O-5Q show Raman spectra and images of 2 common white powders that can easily be differentiated with Raman Chemical Imaging.

DETAILED DESCRIPTION OF THE PREFERRED EMBODIMENTS

Figure 1:
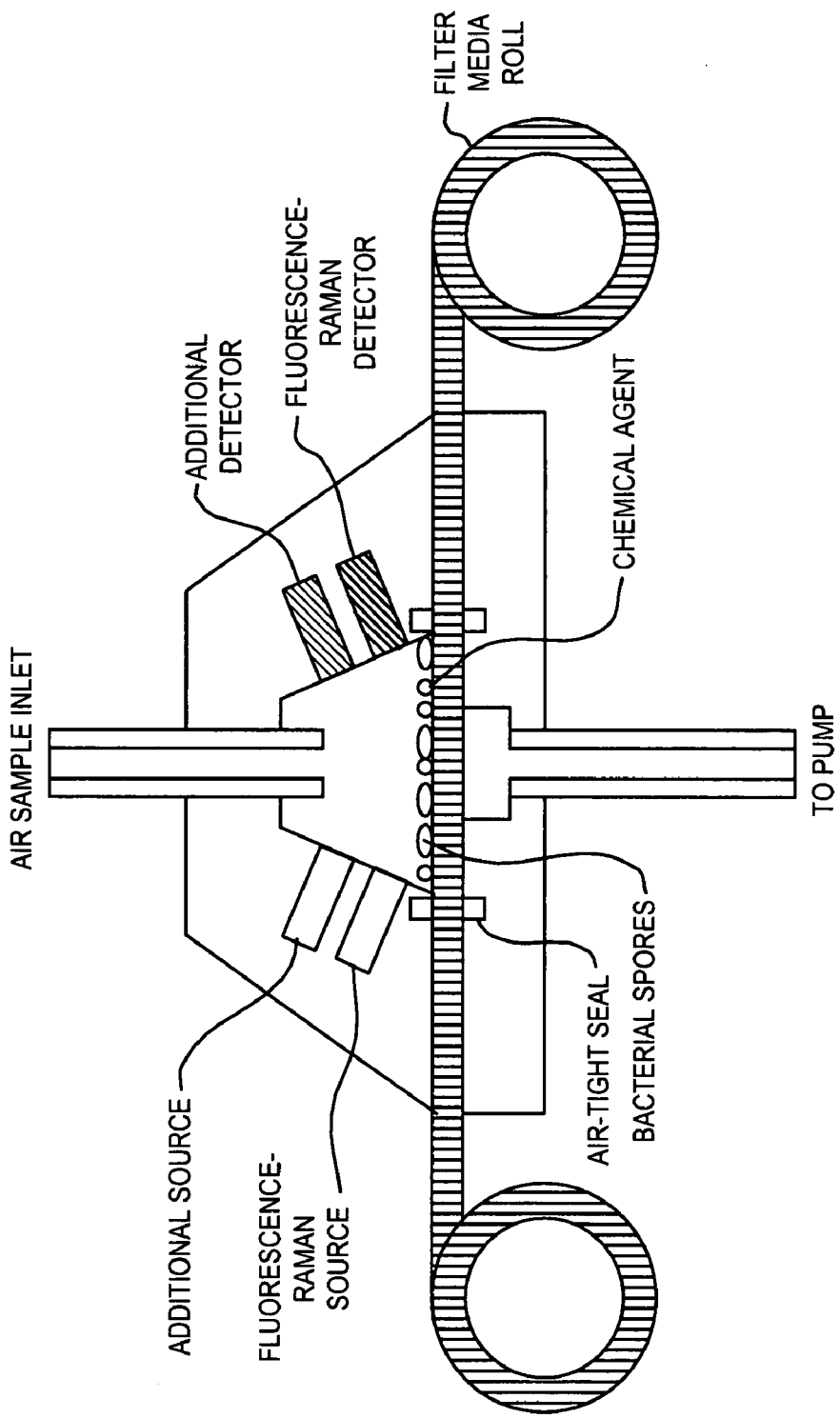
FIG. 1 is a schematic of an ambient air BWA and CWA sensor based on imaging spectroscopic detection.

Methods of Raman chemical imaging are extensively covered in the following US patents and Patent applications assigned to the assignee of the present invention: U.S. Pat. No. 6,002,476; U.S. Non-Provisional application Ser. No. 09/619,371 filed Jul. 19, 2000; U.S. Non-Provisional application Ser. No. 09/800,953 filed Mar. 7, 2001; U.S. Non-Provisional application Ser. No. 09/976,391 filed Oct. 21, 2001; U.S. Non-Provisional application Ser. No. 10/185,090 filed Jun. 27, 2002; U.S. Non-Provisional application Ser. No. 10/184,580 filed Jun. 27, 2002; U.S. Provisional Application 60/144,518 filed Jul. 19, 1999; U.S. Provisional Application No. 60/347,806 filed Jan. 10, 2002; U.S. Provisional Application No. 60/187,560 filed Mar. 28, 2000; U.S. Provisional Application No. 60/239,969 filed Nov. 13, 2000; U.S. Provisional Application No. 60/301,708 filed Jun. 28, 2001; U.S. Provisional Application No. 60/422604 filed Nov. 21, 2002.

The above identified patents and patent applications are hereby incorporated by reference, including referenced material.

Spectroscopy is the study of the interaction of light and matter. Light can be absorbed, reflected, transmitted, emitted or scattered by a substance at characteristic wavelengths (i.e., colors) of the electromagnetic spectrum (incl. gamma ray, X ray, ultraviolet (UV), visible light, infrared, microwave, and radio-frequency radiation) upon excitation by an external energy source. These characteristic wavelengths can then lead to the identification of the material's elemental and/or molecular composition. Experiments typically consist of a light source, a light-dispersing element (i.e., prism or grating) to create a spectrum and a detection device.

In Raman spectroscopy, the photons of interest are scattered by the material. If the incident light is monochromatic (single wavelength) as it is when using a laser source, a small fraction of the scattered radiation differs in frequency (wavelength) from that of the laser. Furthermore, frequencies of the scattered light are unique to the molecular species present. This phenomenon is known as the Raman effect.

In Raman spectroscopy, energy levels of molecules are probed by monitoring the frequency shifts present in scattered light. A typical experiment consists of a monochromatic source (usually a laser) that is directed at a sample. Raman scattering is monitored using instrumentation such as a spectrometer and a charge-coupled device (CCD) detector.

Similar to an infrared spectrum, a Raman spectrum reveals the molecular composition of materials, including the specific functional groups present in organic and inorganic molecules. Raman is useful because each resonance exhibits a characteristic 'fingerprint' spectrum, subject to various selection rules. Peak shape, peak position and the adherence to selection rules can also be used to determine molecular conformation information (crystalline phase, degree of order, strain, grain size, etc.). Unlike infrared spectroscopy, a single Raman spectrometer can be applied to the molecular characterization of organic and inorganic materials simultaneously. Other advantages of Raman over traditional infrared spectroscopy include the ability to analyze aqueous phase materials and the ability to analyze materials with little or no sample preparation. Deterrents to using Raman spectroscopy as opposed to infrared spectroscopy include the relatively weak nature of the Raman phenomenon and interferences due to fluorescence. In the past several years, a number of key technologies have been introduced into wide use that have enabled scientists to largely overcome the problems inherent to Raman spectroscopy. These technologies include high efficiency solid-state lasers, efficient laser rejection filters, and silicon CCD detectors.

In fluorescence spectroscopy, photons are emitted from a material following an excitation step in which absorption of photons occurs. Experiments typically include a polychromatic excitation source such as mercury (Hg) or xenon (Xe) lamps or a monochromatic source such as a laser for sample excitation. A portion of the emitted radiation may then be directed into a dispersive monochromator to which a detector device such as a CCD is attached. By measuring the fluorescence spectrum from a material, one can deduce qualitative and quantitative information from inorganic and organic species. In comparison to Raman spectroscopy, fluorescence is inherently more sensitive. Detection limits in the parts-per-billion are common. On the other hand, fluorescence is less selective than Raman and there are a limited number of chemical systems that exhibit fluorescence.

Molecular UV/visible and NIR absorption spectroscopies involve the absorption of photons throughout the UV/visible (185-780 nm (54,054 to 12,800 $cm^{-1}$) and NIR (780 nm-2.5 μm (12,800 to 4,000 $cm^{-1}$) spectral regions, respectively. Typical instrumentation includes a polychromatic source such as a deuterium or quartz tungsten halogen lamp, a dispersive element such as a monochromator or interferometer and a detection device such as a Si CCD or InGaAs focal plane array detector. Absorption measurements based upon UV-visible or NIR radiation find a wide number of applications for both qualitative and quantitative determination of inorganic and organic species. NIR spectra result from the overtone and combination bands of fundamental mid-infrared (MIR) bands. Like fluorescence, absorption spectroscopies are highly sensitive but only moderately selective.

Spectroscopic methods can be extended to imaging techniques through the use of imaging spectrometers such as liquid crystal imaging spectrometers. The development of this technology in recent years has enabled widefield spectroscopic imaging to develop and mature.

Spectroscopic imaging is a versatile technique that is well suited to the analysis of complex heterogeneous materials. Applications of spectroscopic imaging range from the analysis of polymer blends, defect status analysis in semiconductor materials, inclusions in human breast tissue, characterization of corrosion samples and detection, classification and identification of BWAs and CWAS. Spectroscopic imaging provides a potential solution for obtaining both qualitative and quantitative image information about molecular composition and morphology of BWAs and CWAs allowing a more accurate and more rapid analysis than traditional imaging or 'wet' chemical methods.

Spectroscopic imaging respectively combines Raman, fluorescence, UV/visible absorption/reflectance and NIR absorption/reflectance spectroscopies with digital imaging for the molecular-specific analysis of materials. This enabling technology allows images of samples to be recorded at discrete wavelengths (energies). A spectrum is generated corresponding to millions of spatial locations at the sample surface by tuning the liquid crystal imaging spectrometer over a range of wavelengths and collecting images intermittently. Depending on the materials and the spectroscopic method of choice, depth-related information can also be obtained by using different excitation wavelengths or by capturing spectroscopic images at incremental planes of focus. Contrast is generated in the images based on the relative amounts of Raman scatter, fluorescence emission, UV/visible absorption/reflectance or NIR absorption/reflectance that is generated by the different species located throughout the sample. Since a spectrum is generated for each pixel location, chronometric analysis tools such as correlation analysis, Principal Component Analysis (PCA) and factor rotation, including Multivariate Curve Resolution (MCR) can be applied to the image data to extract pertinent information otherwise missed by ordinary univariate measures.

A spatial resolving power of approximately 250 nm has been demonstrated for Raman spectroscopic imaging using visible laser wavelengths. This is almost two orders of magnitude better than infrared imaging that is typically limited to 20 microns due to diffraction. In addition, image definition (based on the total number of imaging pixels) can be very high for spectroscopic imaging based on liquid crystal optics because of the use of high pixel density detectors (often 1 million plus detector elements).

Instantaneous Anthrax Detection System Based Upon Spectroscopic Imaging Instrumentation There are a number of immediate instrumentation configurations based on spectroscopic imaging that may meet the key instrument requirements outlined previously necessary to be an effective, instantaneous Anthrax detection system. These configurations include platforms based on a microscope, a macroscope, an endoscope, a fiber array spectral translator (FAST), or air sampler designs. Each of these is outlined briefly below.

Microscope-Based System

The spectroscopic imaging microscope combines in a single platform a solid state laser for sample excitation (Raman and laser-induced fluorescence only), a refractive optical microscope base, which is equipped with infinity-corrected microscope objectives, an automated XYZ translational microscope stage and a quartz tungsten halogen (QTH) lamp and/or a mercury (Hg) lamp. Also a part of the microscope system is an analog color charge-coupled device (CDD) detector for ordinary optical image collection and digital image collection, a liquid crystal imaging spectrometer or other imaging spectrometer technology including AOTF, scanned linearly variable or rotated circularly variable dielectric filters, angle-rotated Fabry Perot dielectric or other bandpass filter, interferometers including Michelson and Zhenac types, dispersive spectrometers, or a Computed Tomograph Imaging Spectrometer, for spectroscopic image wavelength selection. Also included is either a room temperature or optionally cooled IR FPA for IR image capture or a thermoelectrically cooled (TE) Si CCD detector for UV/visible, Raman and fluorescence image capture, and a remote, dispersive monochromator equipped with a CDD detector for dispersive spectral collection.

UV, visible or NIR illumination is directed to the sample in a reflected light configuration using a QTH source or other broadband white light source, including metal halide, Hg arc lamps or Xe arc lamps or a transmitted light configuration using QTH or other suitable source of a refractive optical microscope platform. In a Raman or laser-induced fluorescence experiment, laser radiation is introduced to the sample through use of a Raman illuminator. Light scattered, emitted, reflected or transmitted is collected from the sample positioned on the automated XYZ translational microscope stage through an infinity-corrected microscope objective.

Ordinary optical imagery of the sample can be obtained using a mirror or beamsplitter or prism arrangement inserted into turret wheel of the microscope and collecting an image with an analog or digital color or monochrome charge-coupled device (CCD) or CMOS detector. In spectroscopic imaging mode, the magnified spectroscopic image is coupled through an imaging spectrometer and collected on a NIR or mid-IR focal plane array (FPA) detector (for IR spectroscopic imaging) or a Si CCD detector (for UV/visible absorption/reflectance, fluorescence and Raman spectroscopic imaging. The IR FPA is typically comprised of indium gallium arsenide (InGaAs), but may be comprised of other IR sensitive materials, including platinum silicide (PtSi), indium antimonide (InSb) or mercury cadmium telluride (HgCdTe).

A central processing unit, typically a Pentium computer, is used for spectroscopic image collection and processing. The analog color CCD, IR FPA and/or Si CCD, automated XYZ translational microscope stage controlled via a controller and liquid crystal or other imaging spectrometer (through the appropriate imaging spectrometer controller) are operated with commercial software, such as ChemAcquire (ChemImage Corporation) in conjunction with ChemAnalyze (ChemImage Corporation).

By introducing a polarization sensitive beam splitting element in the optical path prior to the liquid crystal imaging spectrometer, a portion of the signal from the sample may be coupled to a remote dispersive spectrometer. This allows conventional spectroscopic tools to be used to gather spectra for traditional, high-speed spectral analysis. The spectrometers can be of the following types: fixed filter spectrometers; grating based spectrometers; Fourier Transform spectrometers; or Acousto-Optic spectrometers. A polarization independent interferometer such as a: Michelson interferometer, Sagnac interferometer; Twynam-Green Interferometer, Mach-Zehnder Interferometer, may be used as a filter.

Preferably, liquid crystal (LC) imaging spectrometer technology is used for wavelength selection. The LC imaging spectrometer may be of the following types: Lyot liquid crystal tunable filter (LCTF); Evans Split-Element LCTF; Solc LCTF; Ferroelectric LCTF; Liquid crystal Fabry Perot (LCFP); or a hybrid filter technology comprised of a combination of the above-mentioned LC filter types. Additionally, fixed bandpass and bandreject filters comprised of dielectric, rugate, holographic, color absorption, acousto-optic or polarization types may also be used, either alone or in combination with one of the above LC spectrometers.

The spectroscopic imaging microscope can be used as a volumetric imaging instrument through the means of moving the sample through focus in the Z, axial dimension, collecting images in and out of focus and reconstructing a volumetric image of the sample in software. For samples having some volume (bulk materials, surfaces, interfaces, interphases), volumetric spectroscopic imaging has been shown to be useful for failure analysis, product development and routine quality monitoring. The potential also exists for performing quantitative analysis simultaneous with volumetric analysis. Volumetric imaging can be performed in a non-contact mode without modifying the sample through the use of numerical confocal techniques, which require that the sample be imaged at discrete focal planes. The resulting images are processed, reconstructed, and visualized. Computational optical sectioning reconstruction techniques based on a variety of strategies have been demonstrated, including nearest neighbors and iterative deconvolution.

Microscope-based spectroscopic imaging systems have the distinct image of being able to detect, classify, identify and visualize BWAs down to a single bacterium for instance. These systems boast a spectral resolution on the order of 8 $cm^{-1}$ and a spatial resolution of approximately 200 nm with numerical deconvolution methods.

Macroscope-Based System

The spectroscopic imaging macroscope combines in a single platform and illumination subassembly consisting of an illumination source (typically a QTH, Xe, Hg or other metal halide lamp), barrier optical filter(s) and a light-directing module (i.e., direct beam, fiber optic or liquid light guide illumination). An analog color charge-coupled device (CCD) detector is used for ordinary optical and digital image collection. Wavelength selection is done using a liquid crystal imaging spectrometer or other imaging spectrometer. The imaging detector is either a room temperature or optionally cooled NIR FPA for NIR image capture or a thermoelectrically cooled (TE) Si CCD detector for UV/visible and fluorescence image capture.

UV,visible or NIR illumination is directed to the sample in a reflected light configuration using a QTH source or other broadband white light source, including metal halide, Hg arc lamps or Xe arc lamps or a transmitted light configuration using QTH or other suitable source through direct illumination, fiber optics or liquid light guides. Light emitted, reflected or transmitted is collected from the sample positioned on the macroscopic sample base through a macro lens.

Ordinary optical imagery of the sample may be obtained using a mirror or beamsplitter or prism arrangement inserted into the collection stack of the macroscope and collecting an image with an analog or digital color or monochrome charge-coupled device (CCD) or CMOS detector. In spectroscopic imaging mode, the spectroscopic image is coupled through a liquid crystal imaging spectrometer and collected on a NIR focal plane array (FPA) detector (for NIR spectroscopic imaging) or a Si CCD detector (for UV/visible absorption/reflectance, fluorescence and Raman spectroscopic imaging). The NIR FPA is typically comprised of indium gallium arsenide (InGaAs), but may be comprised of other NIR sensitive materials, including platinum silicide (PtSi), indium antimonide (InSb) or mercury cadmium telluride (HgCdTe).

A central processing unit, typically a Pentium computer, is used for spectroscopic image collection and processing. The analog color CCD, NIR FPA and/or Si CCD and liquid crystal imaging spectrometer or other imaging spectrometer (through an appropriate imaging spectrometer controller) are operated with commercial software, such as ChemAcquire (ChemImage Corporation) in conjunction with ChemAnalyze (ChemImage Corporation.).

Preferably, liquid crystal (LC) imaging spectrometer technology is used for wavelength selection. The LC imaging spectrometer may be of the following types: Lyot liquid crystal tunable filter (LCTF); Evans Split-Element LCTF; SoIc LCTF; Ferroelectric LCTF; Liquid crystal Fabry Perot. (LCFP); or a hybrid filter technology comprised of a combination of the above-mentioned LC filter types. Additionally, fixed bandpass and bandreject filters comprised of dielectric, rugate, holographic, color absorption, acousto-optic or polarization types may also be used, either alone or in combination with one of the above LC spectrometers.

The use of a macroscopic-based system has the advantage of enabling rapid detection of potential BWAs and CWAs over a large area. Previous work has shown the ability image 0.01 mm defects on 200 mm semiconductor wafers using the macroscope system.

Endoscope-Based System

Spectroscopic imaging has traditionally been performed in laboratory settings using research-grade light microscope technology as the image-gathering platform. However, spectroscopic imaging is also applicable to in situ industrial process monitoring and in vivo clinical analysis. The application of spectroscopic imaging outside the research laboratory has been limited by the lack of availability of stable imaging platforms that are compatible with the physical demands of industrial process monitoring and clinical environments. Both industrial and clinical settings often require compact, lightweight instrumentation suitable for the examination of remote areas that are inaccessible to conventional spectroscopic imaging instrumentation.

A robust spectroscopic imaging design employing liquid crystal technology has been developed. The liquid crystal endoscope is the first flexible imaging endoscopic technology that provides real-time video inspection capability with spectral analysis. The endoscope, comprising from two to thousands of independent fibers arranged in a coherent imaging bundle, couples to a video CCD for real-time video imaging of the analysis area. This allows for quick visual screening of the sample. The endoscope tip has been engineered to filter both laser illumination and collected Raman scatter and fluorescence emission (for Raman and fluorescence applications). The light from the laser delivery fiber is filtered so that only the laser wavelength is presented to the sample. The laser is removed from the collected light so that Raman information is visible to within 200 $cm^{-1}$ of the laser line. The distal end of the liquid crystal Raman endoscope is environmentally resistant and can withstand continuous operation at high temperatures and has been demonstrated to operate from 0-315.° C. while maintaining high signal to background (S/B) performance. The distal end can be coupled to a microscope-based system enabling dispersive spectroscopy and spectroscopic imaging to be performed remotely.

The use of an endscopic-based spectroscopic imaging system has the advantage of being able to detect the presence of suspect BWAs and CWAs in remote locations such as inside a box or envelope.

FAST-Based System

An emerging technology in the field of spectroscopic imaging is the use of fiber optic arrays. We have termed this technology Fiber Array Spectral Translators (FAST) but it is also described as dimension reduction arrays. FAST technology can acquire a few to thousands of full spectral range, spatially resolved spectra simultaneously. This is done by focusing a spectroscopic image onto a two dimensional array of optical fibers that are drawn into a one-dimensional distal array with serpentine ordering. The one dimensional fiber stack is coupled to an imaging spectrograph. Software then extracts the spectral/spatial information that is embedded in a single CCD image frame. Fiber array spectroscopic imaging has been demonstrated in several applications including Raman chemical imaging analysis of micro-composites and biomaterials and time-resolved atomic emission chemical imaging of laser-induced plumes.

The fundamental advantage of this method over other spectroscopic imaging methods is speed of analysis. A complete spectroscopic imaging data set can be acquired in the amount of time it takes to generate a single spectrum from a given material. A current limitation of FAST is the low image definition (number of image pixels) in the object field. Image definition is dictated by the number of elements in the long axis direction of the detector. Alternatives to current designs can include the use of multiple detectors, which has the potential to increase the image definition. Even with limited pixel definition, superimposing color-coded spectroscopic images on high-spatial resolution gray-scale images can provide significant insight into the morphology and chemistry of materials.

Ambient Air Sensor System

The ambient air sensor system consists of two parts, a sampling system and a spectroscopic imaging system. The key to the sampling system is the optics block, shown diagrammatically in FIG. 1. This block must support a section of filter medium and provide a complete airtight seal around. the periphery of the sampling area. This block must also be easily opened so that either a new filter (discrete filters) or a new section of filter (continuous filters) can be placed in the sampling/optics path.

The sampling system has an inlet, which is open to the atmosphere being tested. Its dimensions are optimized for the sampling flow rate and the anticipated range of particle sizes. For particulate or aerosol sampling, it is important that the inlet have no sharp bends or areas of low linear velocity, which can cause deposition of particulate prior to the collection filter. The sampling system also has a sampling pump, providing the vacuum to pull ambient air through the filter. Anticipated flow rates are in the 0.5 to 2.0 L/min range, and the expected vacuum is in the 100 in.-$H_2O$ (180 mm-Hg) range.

The sampling system is typically not run continuously but rather in a series of discrete sampling periods. At the end of each period, it might be necessary to replace the filter medium. This can be done either by the operator or automatically. For continuous sampling, the filter medium can be in a tape-like configuration and new samples of filter can be positioned in the optics block by a tape-drive mechanism, similar to that of an audiocassette.

Once the particulates have been trapped on the filter medium, imaging spectroscopy is used to detect and classify the BWA or CWA present. If the excitation source is a laser, coupled to the optics block using conventional or fiber optics, whose light is evenly distributed over the whole sampling area, Raman imaging can be used. In another configuration, a light source comprised of a broadband UV/Vis, filtered UV/Vis, or a UV/Vis laser can be used to excite autofluorescence. The imaging detector can be of the liquid crystal tunable type or another imaging spectrometer type as described earlier and a CCD or other array camera can be used to image the sampling area at multiple wavelengths. Coupling of the detector to the optics block can be through fiber-based or conventional optics. The detector data is processed using chronometric and image analysis tools such as those found in the ChemAnalyze software (ChemImage Corporation).

The typical operating mode of this type of ambient air monitor is usually as a series of sampling periods during which periodic spectroscopic image measurements are taken. The results from the previous and current sampling periods are interpreted by a system computer which can display results and activate warning and danger alarms, or initiate some action such as turning off a building outside air intake.

RESULTS

Figure 2:
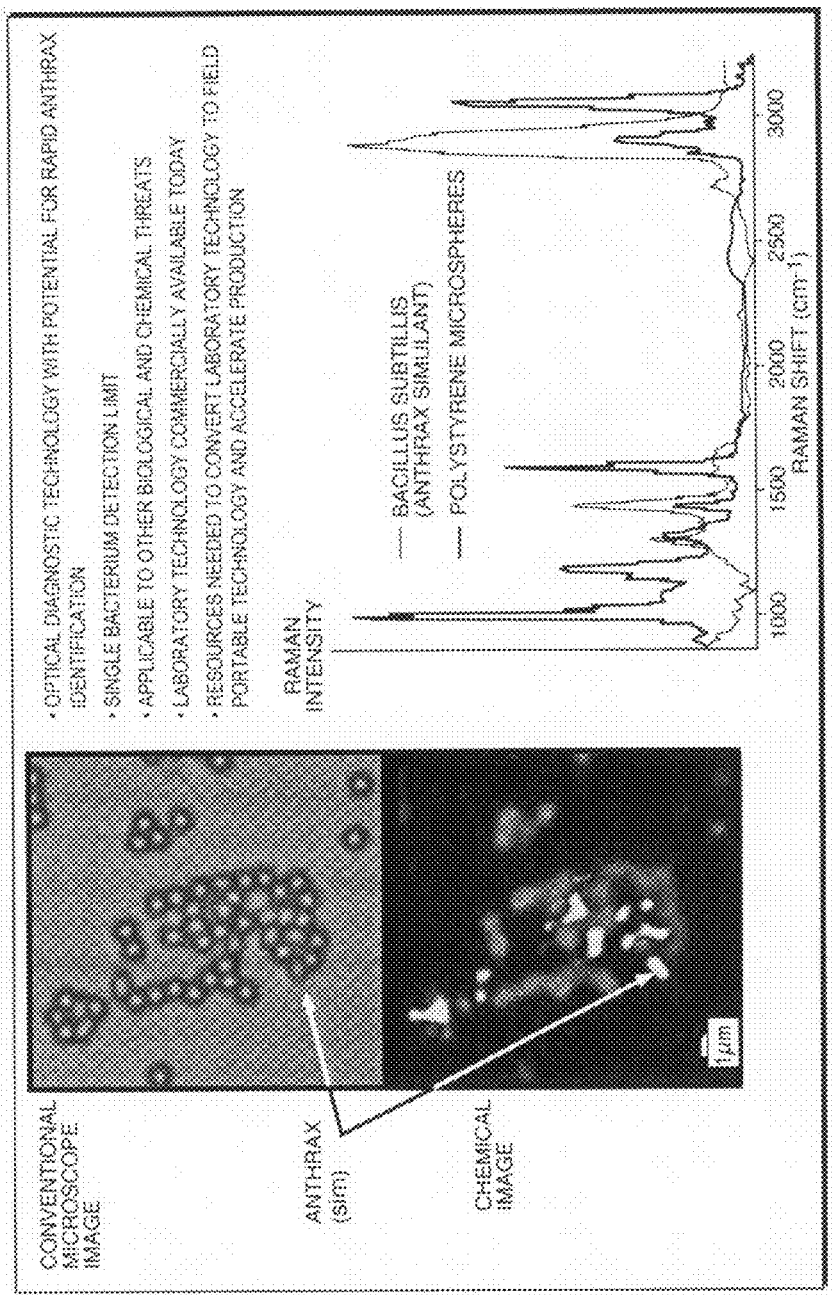
FIG. 2 is a Raman spectroscopic imaging of a mixture of 1 .mu.m diameter polystyrene micro-spheres and *Bacillus subtilis* var. *niger* spores (also known as *Bacillus globigii* (BG) which is an Anthrax simulant).
Figure 3:
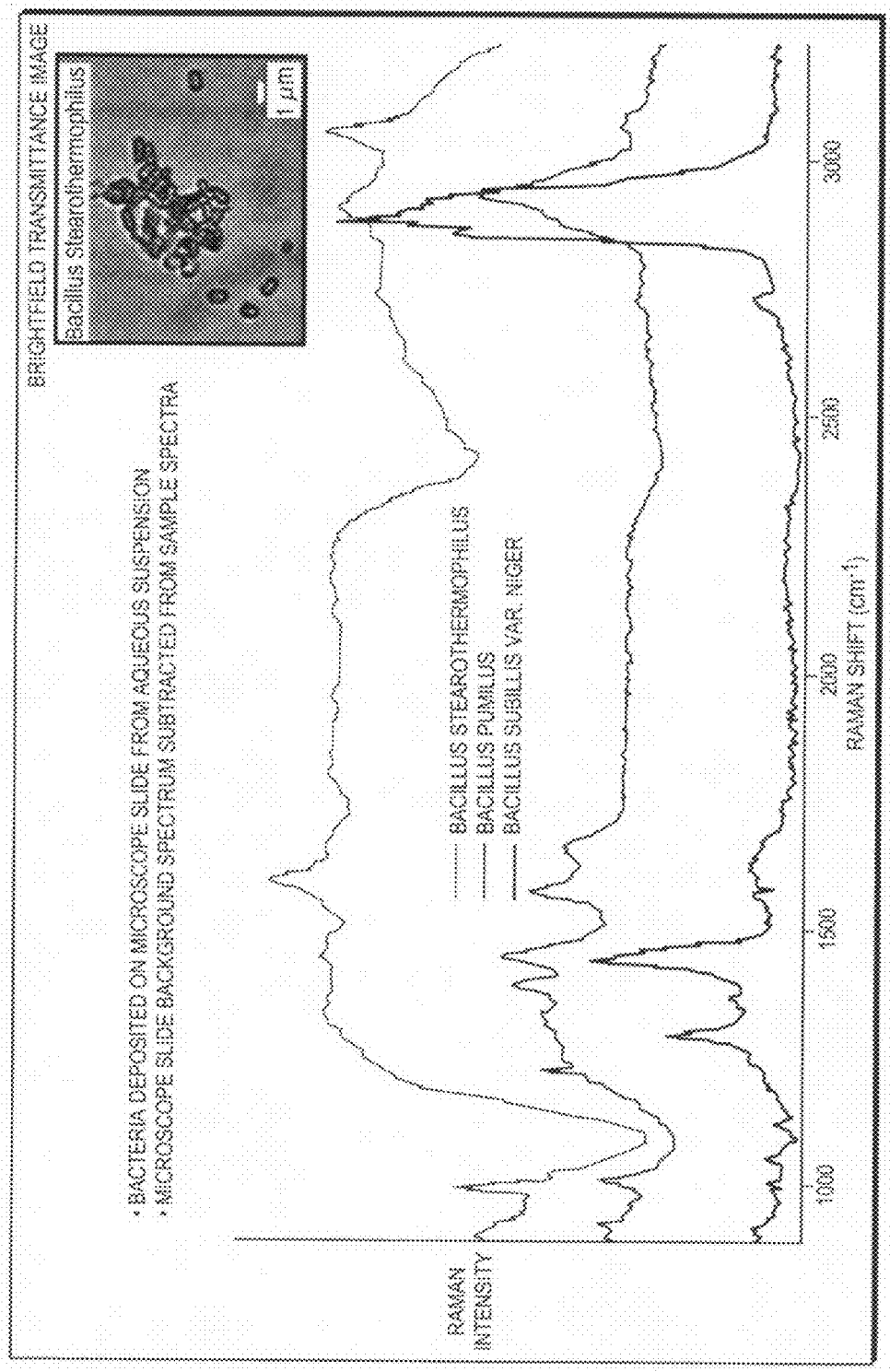
FIG. 3 shows dispersive Raman spectra of three different bacterial spore types including an Anthrax simulant.

Spectra generated using traditional spectroscopic methods can potentially reveal a wealth of information about molecular properties of BWAs and CWAS. Spectroscopic imaging compounds this information by allowing variations in the composition of these materials to be probed downed to a single bacterium if necessary. FIG. 2 shows Raman spectroscopic imaging data on a mixture of 1 .mu.m diameter polystyrene micro-spheres and *Bacillus subtilis* var. *niger* spores (Anthrax simulant). The images on the left side of the figure show a brightfield reflectance image (top) and a Raman spectroscopic image (bottom) of the bacteria spores/micro-spheres mixture. The bacteria spores and micro-spheres have been color-coded green and red, respectively. The Raman spectra to the right of the images show the spectral "fingerprints" associated with the bacteria spores and the polystyrene micro-spheres, respectively. Despite the morphological similarities between the mixture components, the Raman spectroscopic image reveals the molecularly distinct species. This ability to characterize bacteria spores in the presence of non-threatening 'masking' agents is a critical issue in the detection and identification of BWAs and CWAs. Difficulties exist when trying to differentiate spores from different bacterial species. FIG. 3 shows dispersive Raman spectra of three different bacterial spores types. Despite the genetic and morphological similarities, Raman dispersive spectroscopy has been used to sufficiently discriminate among the different bacteria spores.

Figure 4:
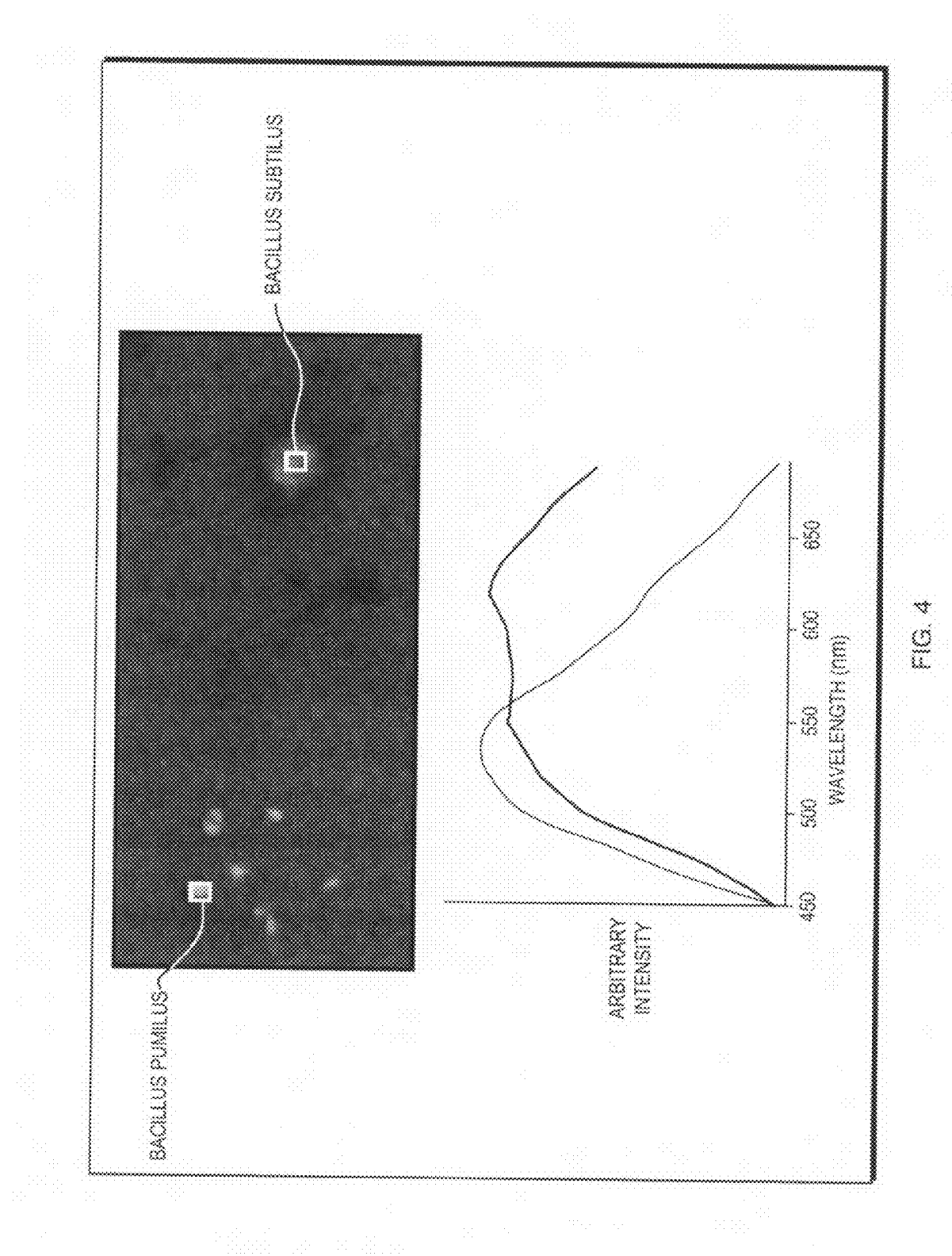
FIG. 4 is a microscopic fluorescence-spectroscopic image of two different bacterial spore types, *Bacillus pumilis* and *Bacillus subtilis*.

FIG. 4 shows how fluorescence spectroscopic imaging can be used to distinguish between bacteria spore types. The fluorescence spectra in the lower portion of the figure were obtained from the color-coded boxed regions in the concatenated fluorescence spectroscopic images above. It can be seen that *Bacillus subtilis* spores and *Bacillus pumilus* spores exhibit fluorescence peaks maxima at 540 nm and 630 nm, respectively.

Figure 5A:
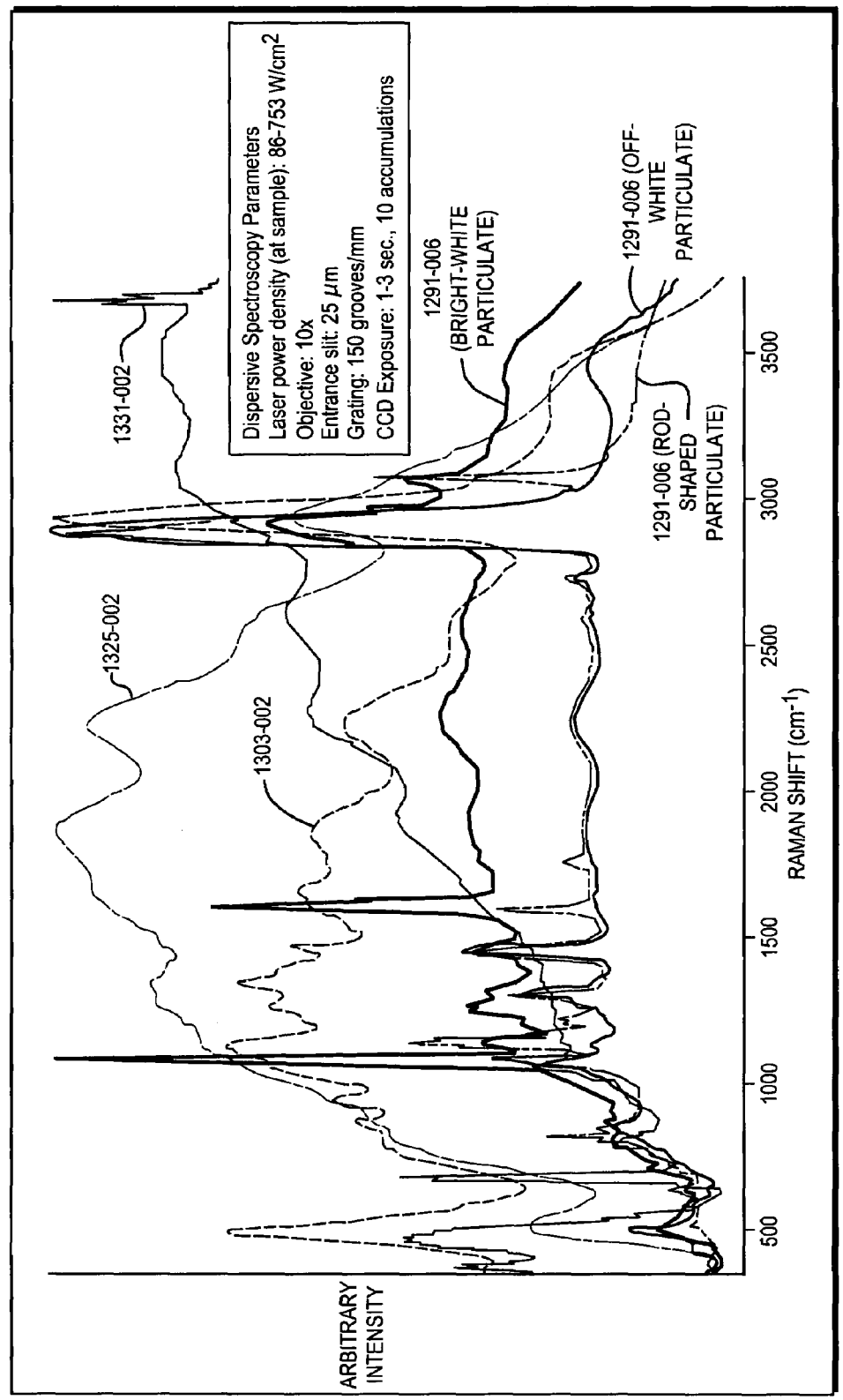
FIG. 5A shows Raman spectra (green laser excitation) of the 6 unidentified powders through the vials.
Figure 5B:
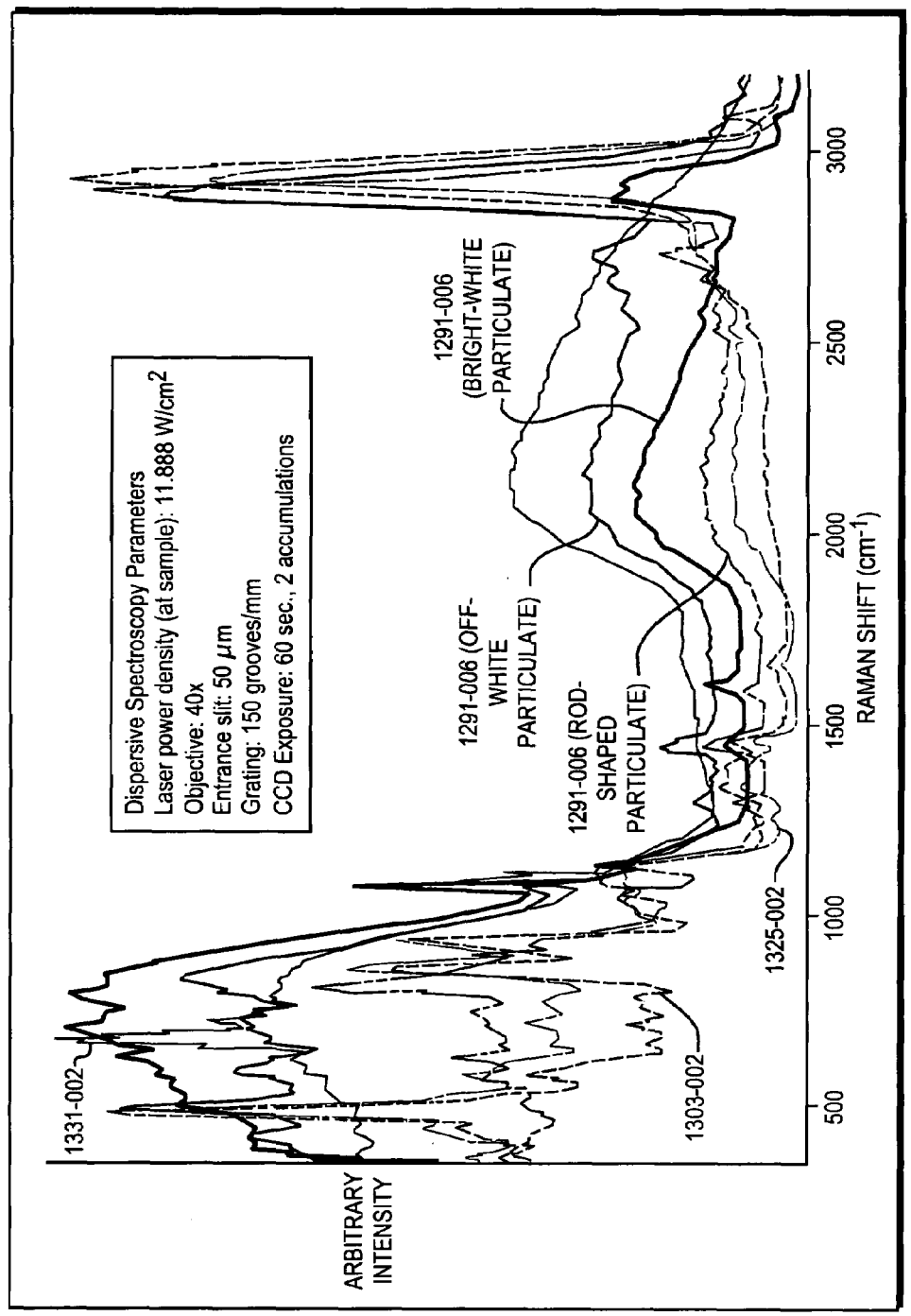
FIG. 5B shows Raman spectra (red laser excitation) of the 6 unidentified powders.
Figure 5C:
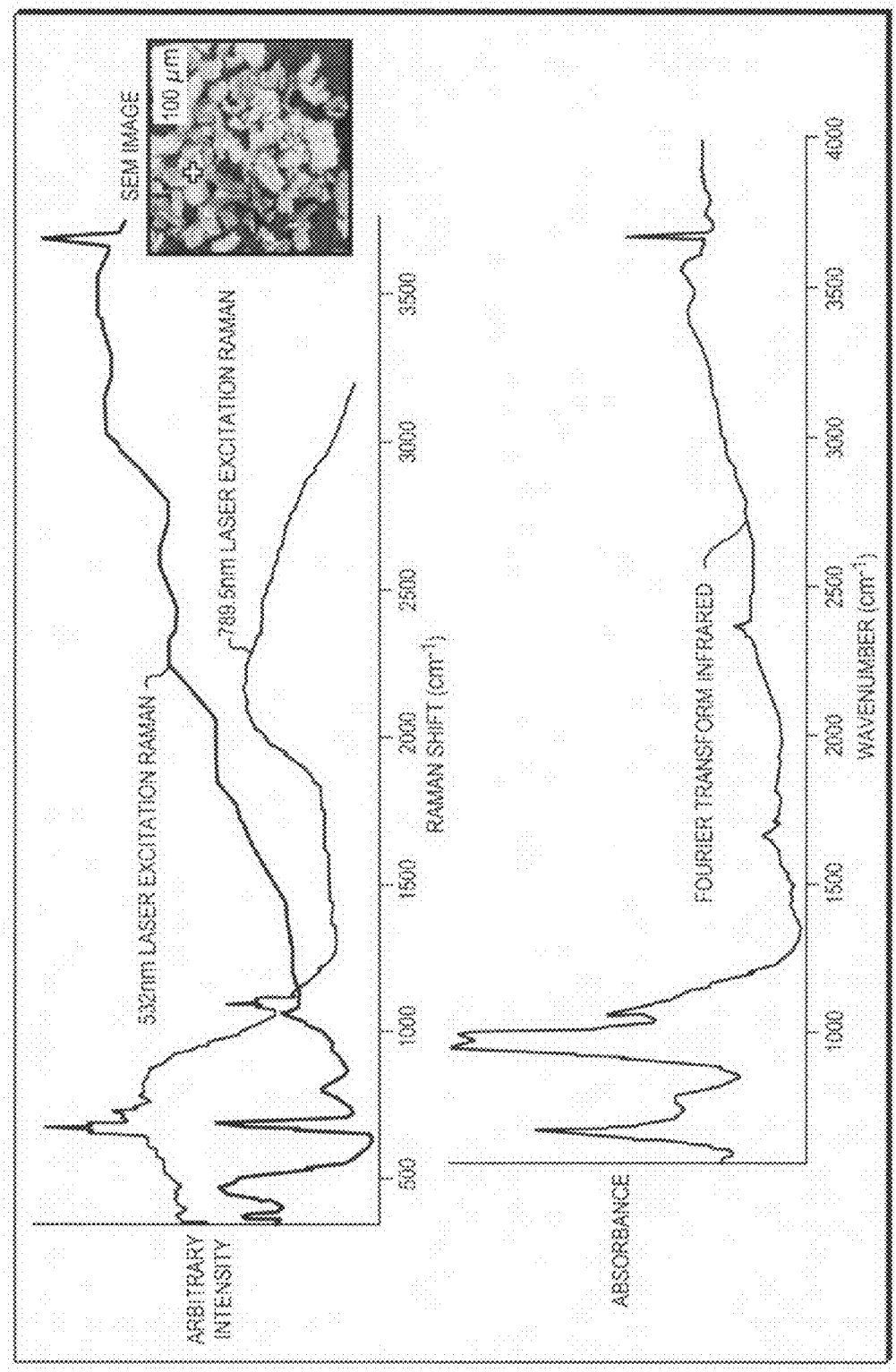
FIGS. 5C-5D (Sample 1331-002) show Raman, IR and SEM-EDS results on a first of the 6 unidentified powders. The sample is inorganic and most likely talc.
Figure 5D:
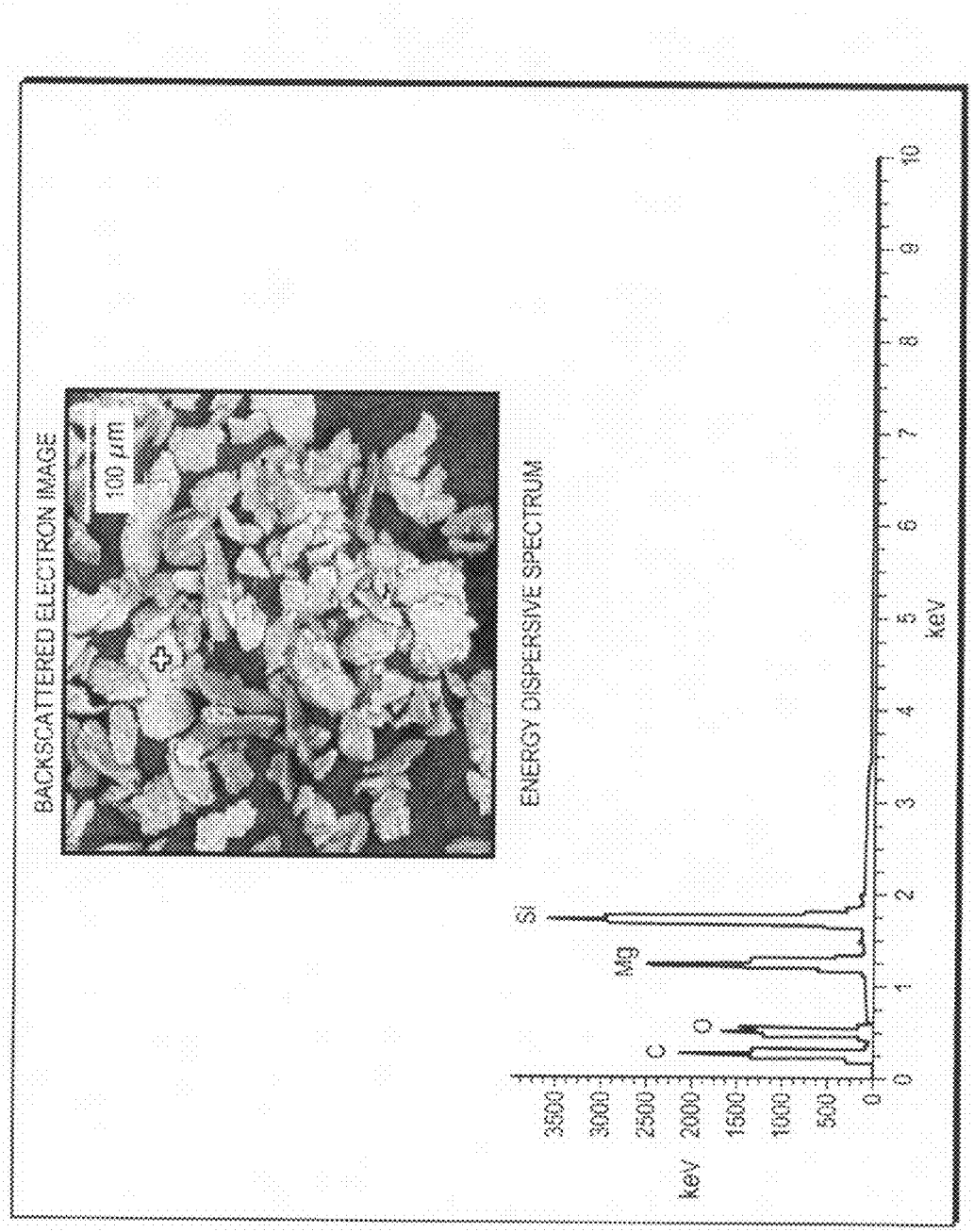
Figure 5E:
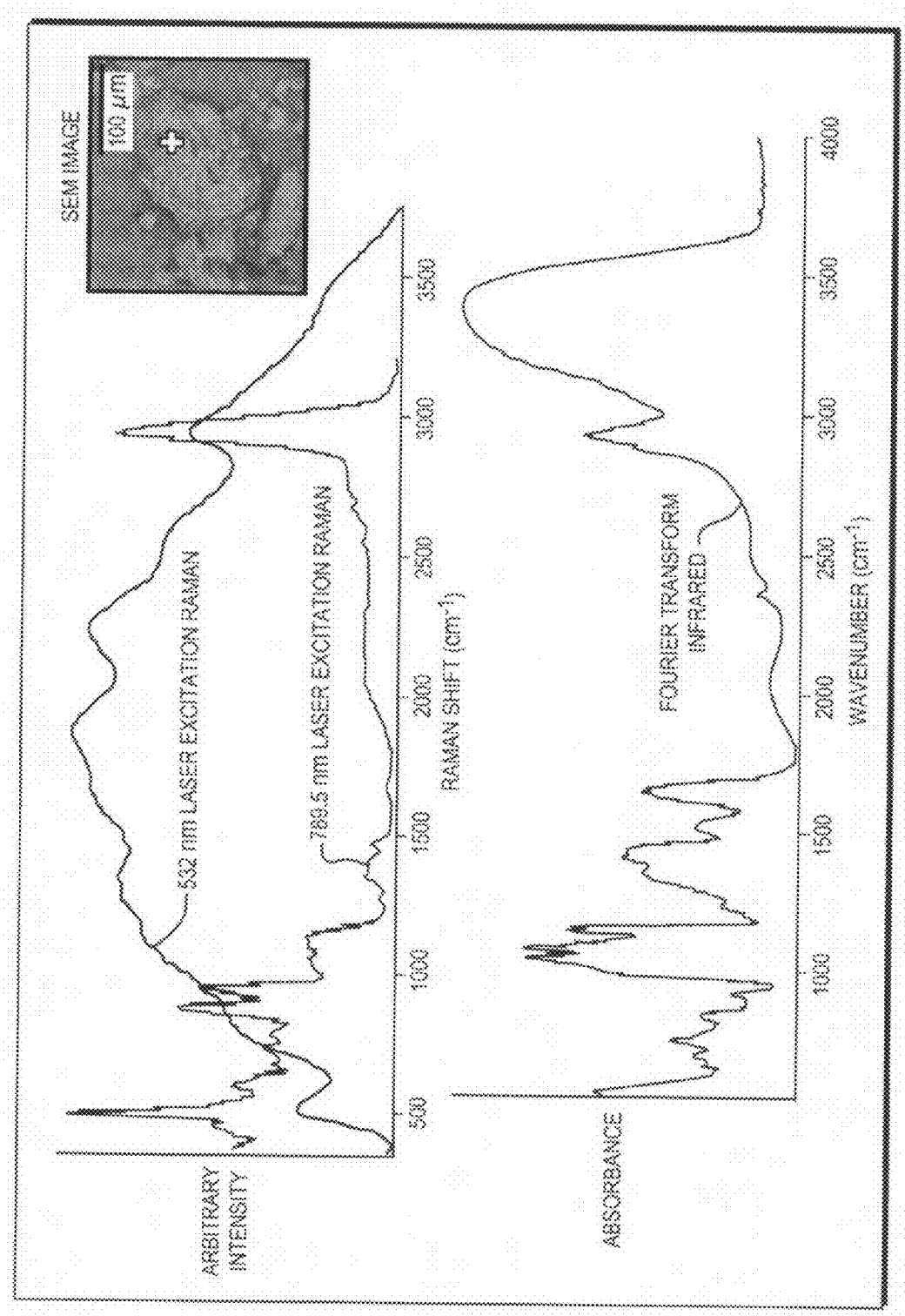
FIGS. 5E-5F (Sample 1325-002) show Raman, IR and SEM-EDS results on a second of the 6 unidentified samples. The sample is organic and most likely starch, possibly corn starch.
Figure 5F:
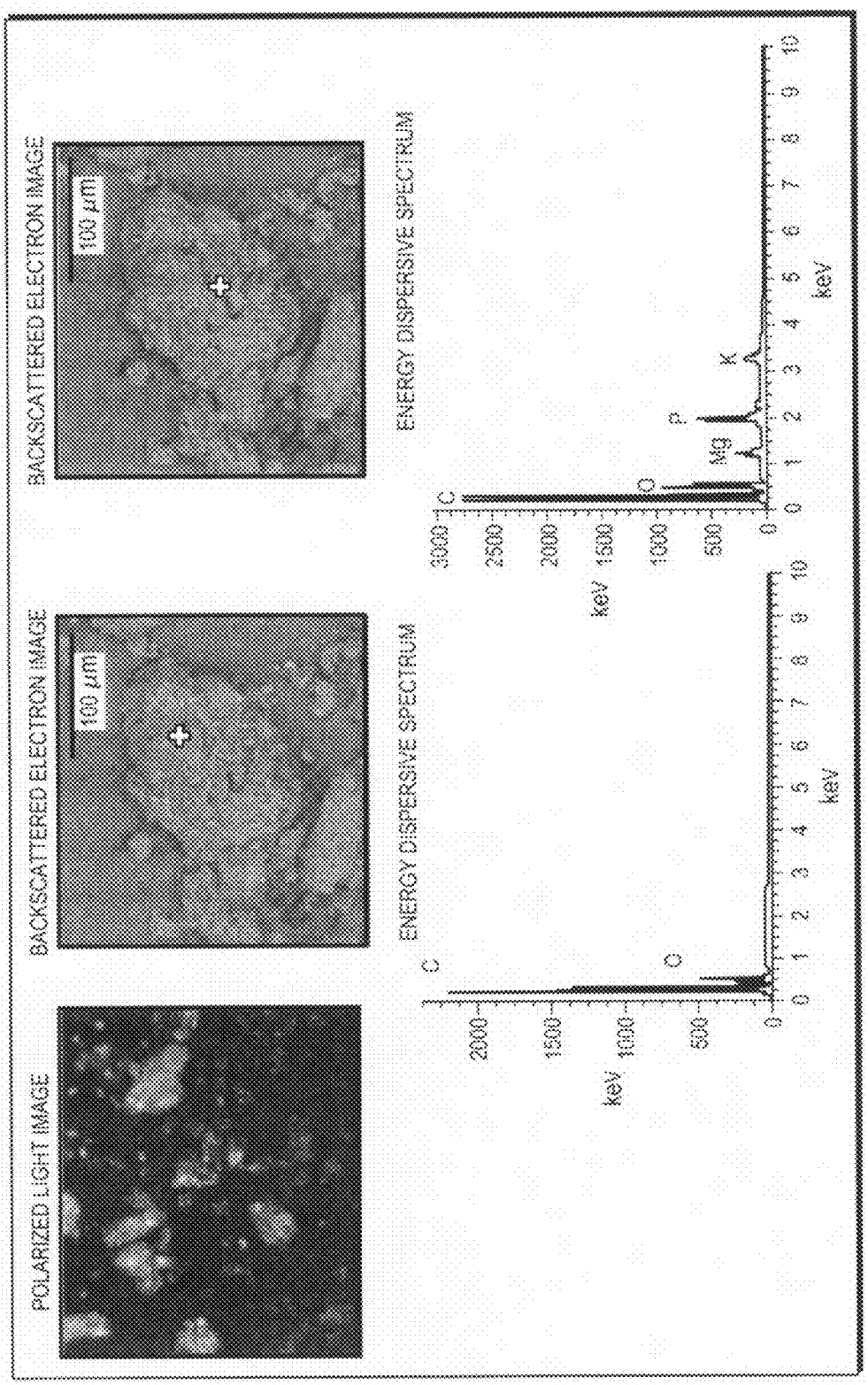
Figure 5G:
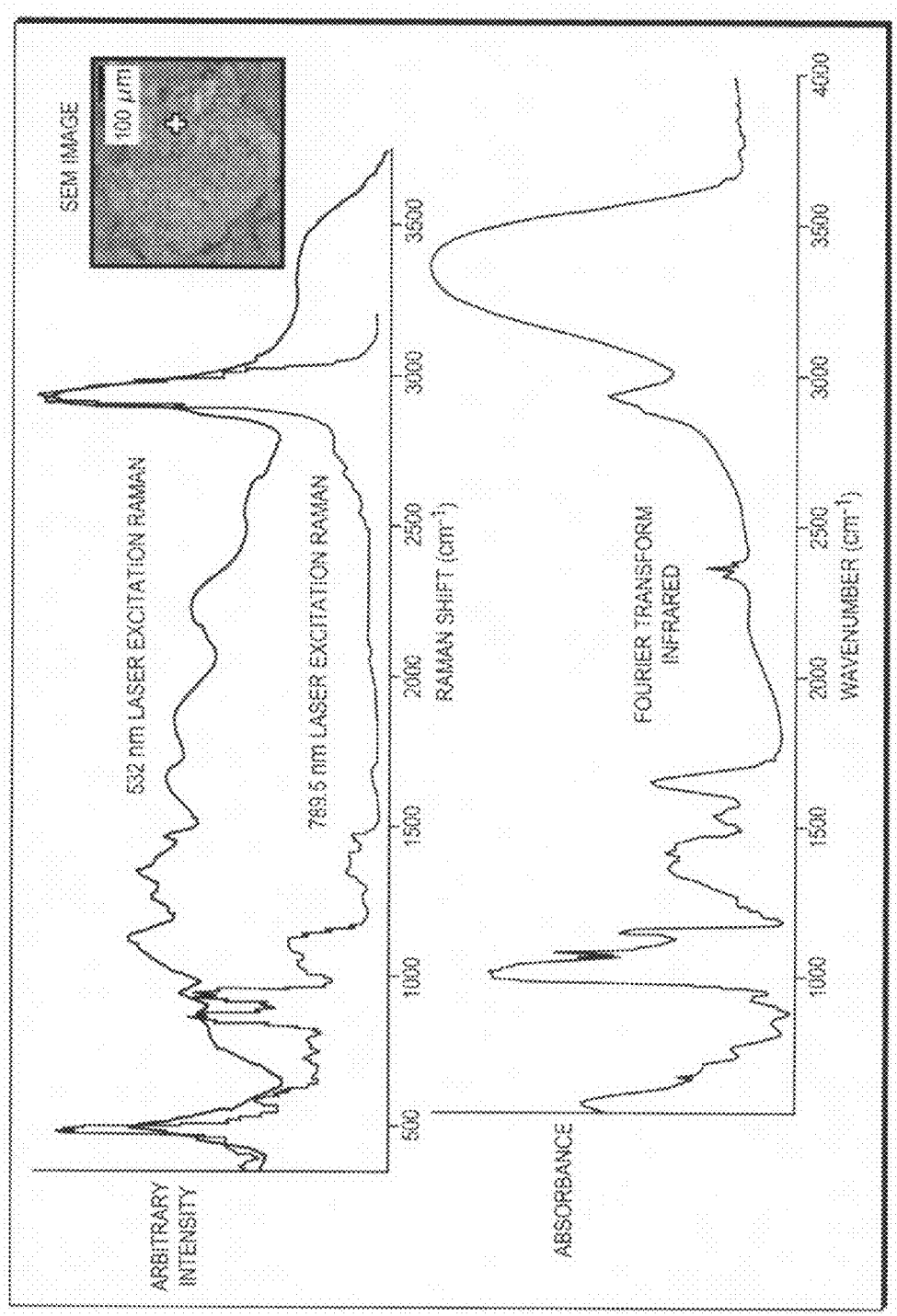
FIGS. 5G-5H (Sample 1303-002) show Raman, IR and SEM-EDS results on a third of the 6 unidentified powders. The sample is organic and most likely starch, possibly corn starch.
Figure 5H:
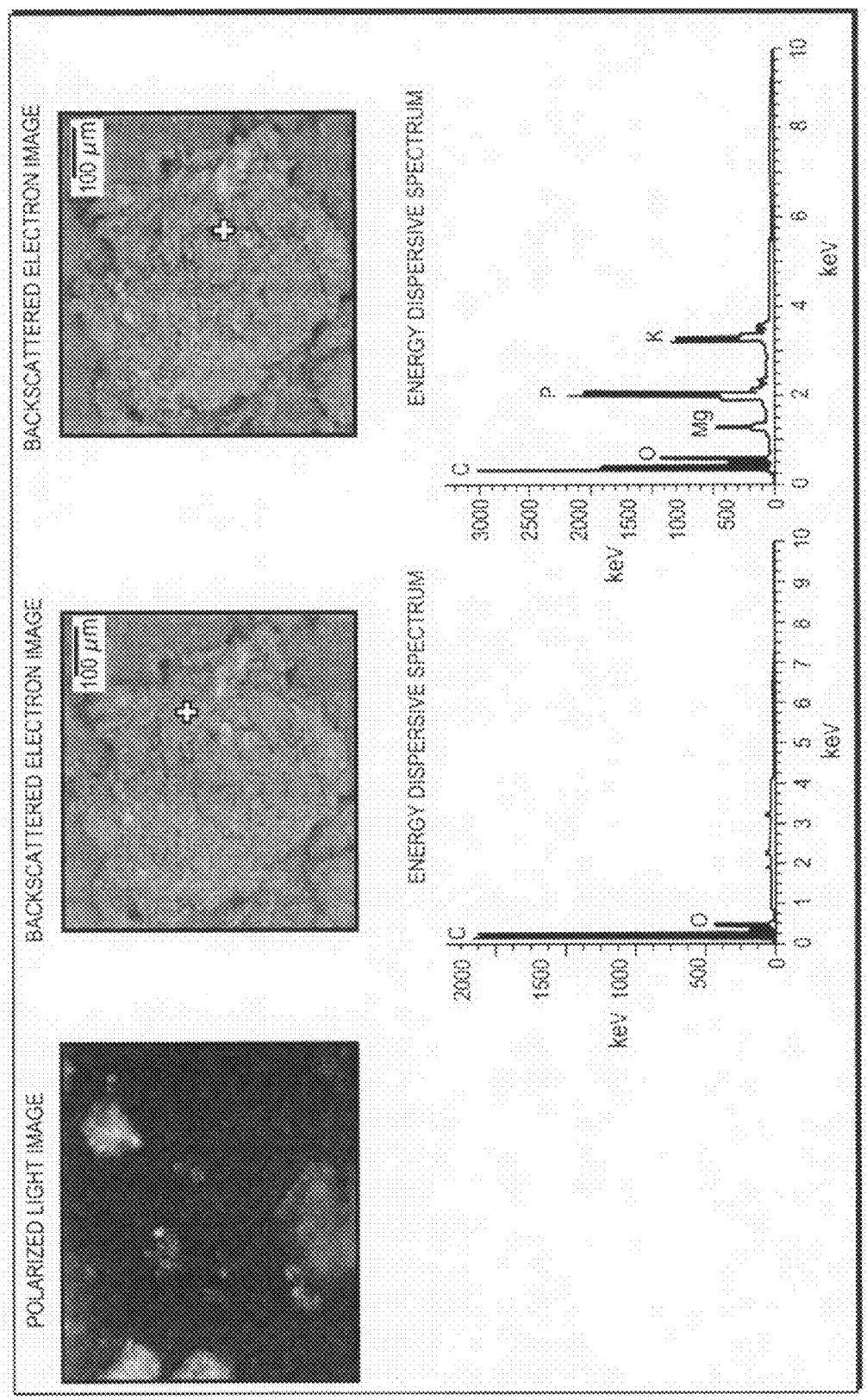
Figure 51:
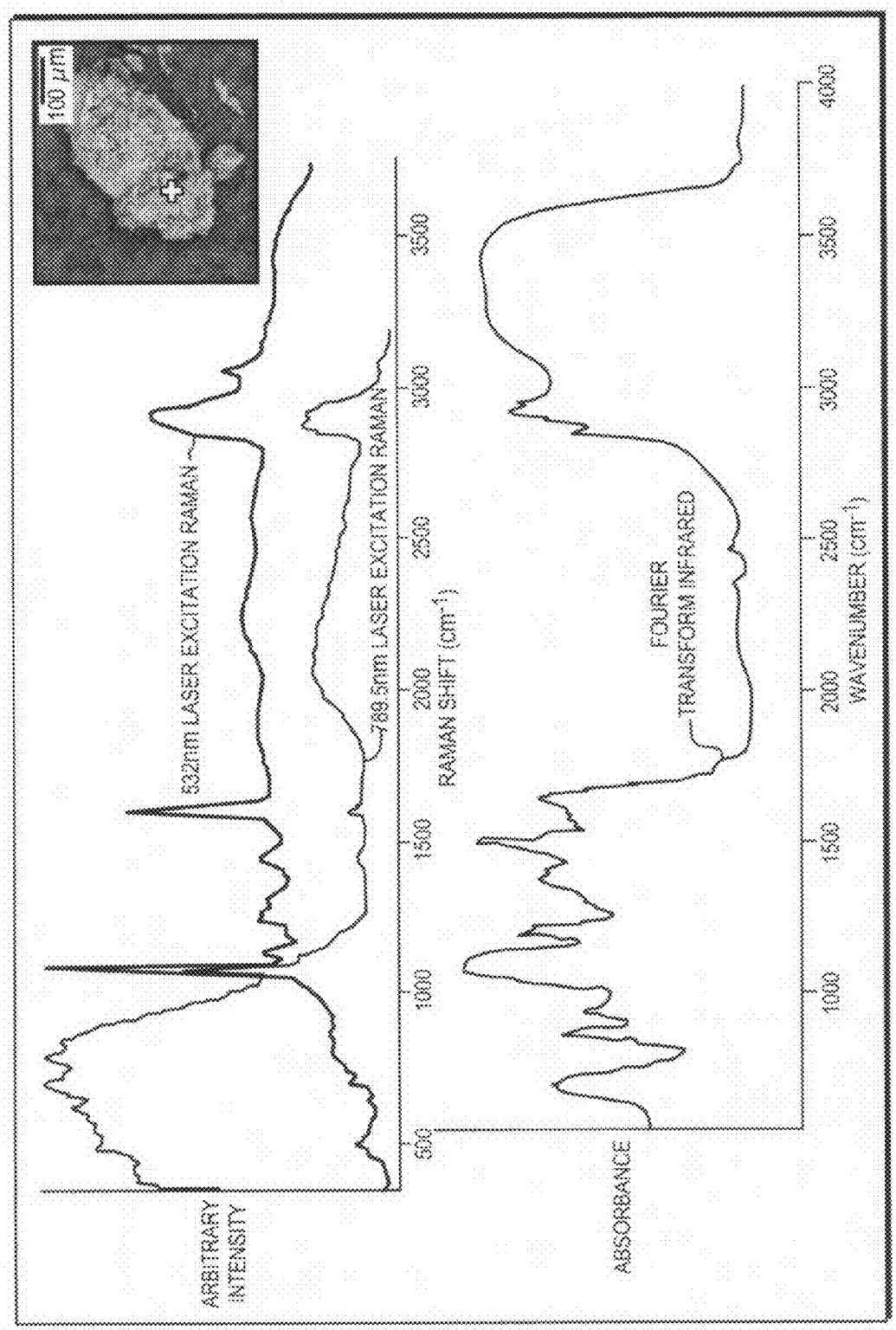
Figure 5J:
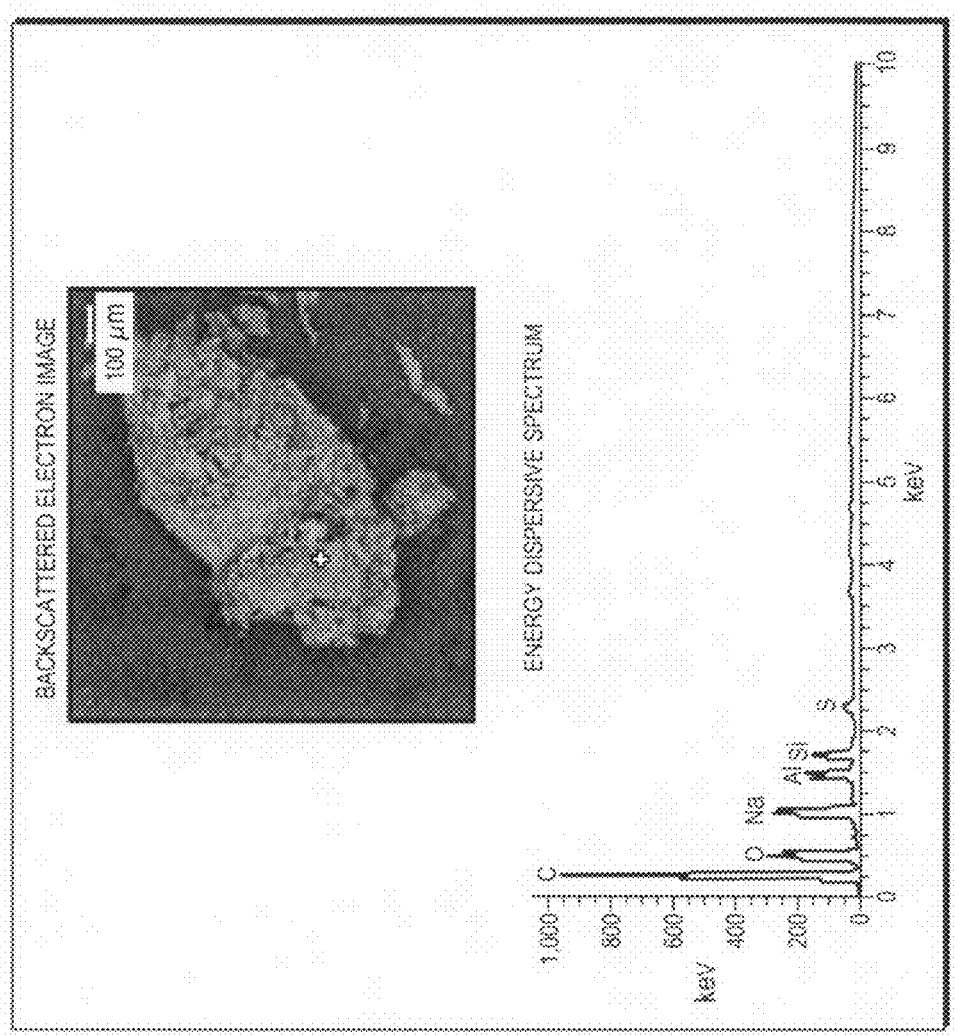
Figure 5K:
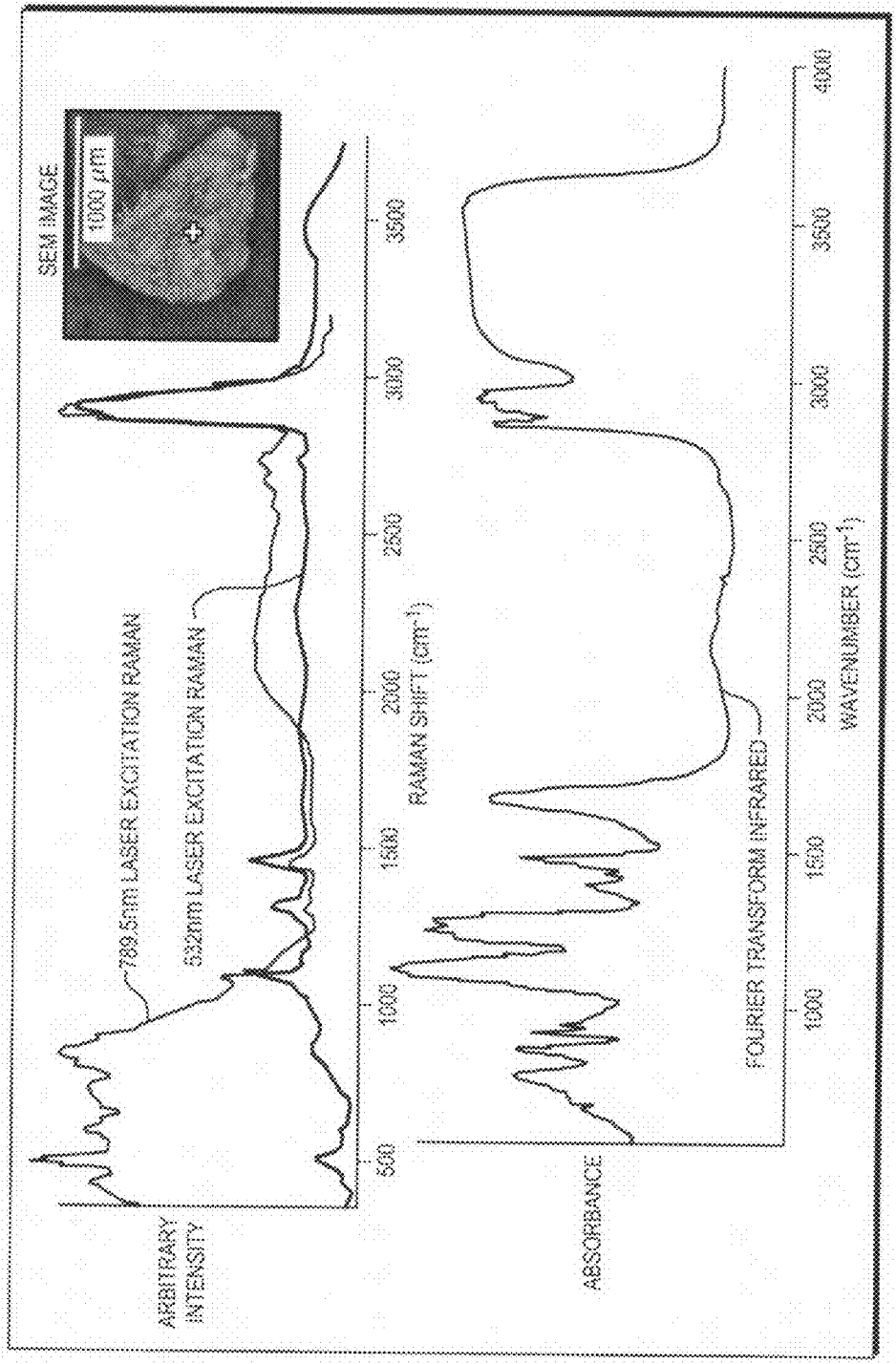
Figure 5L:
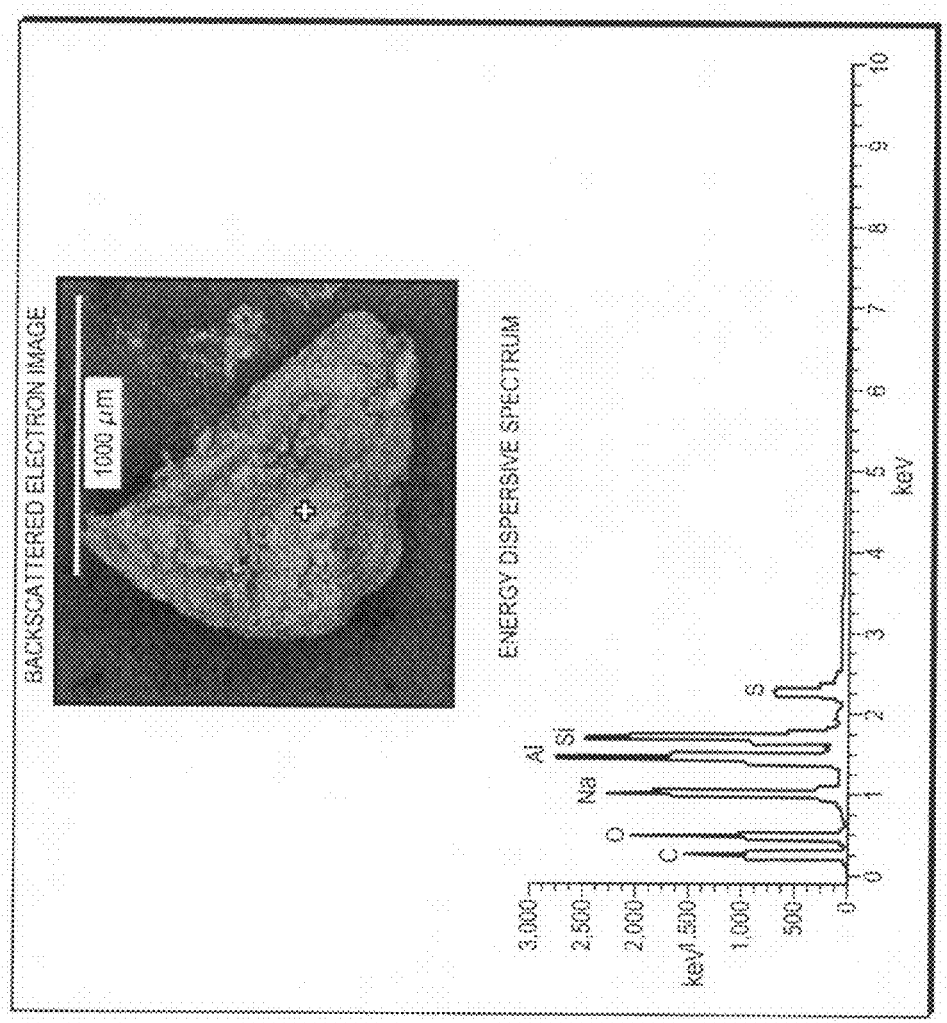
Figure 5M:
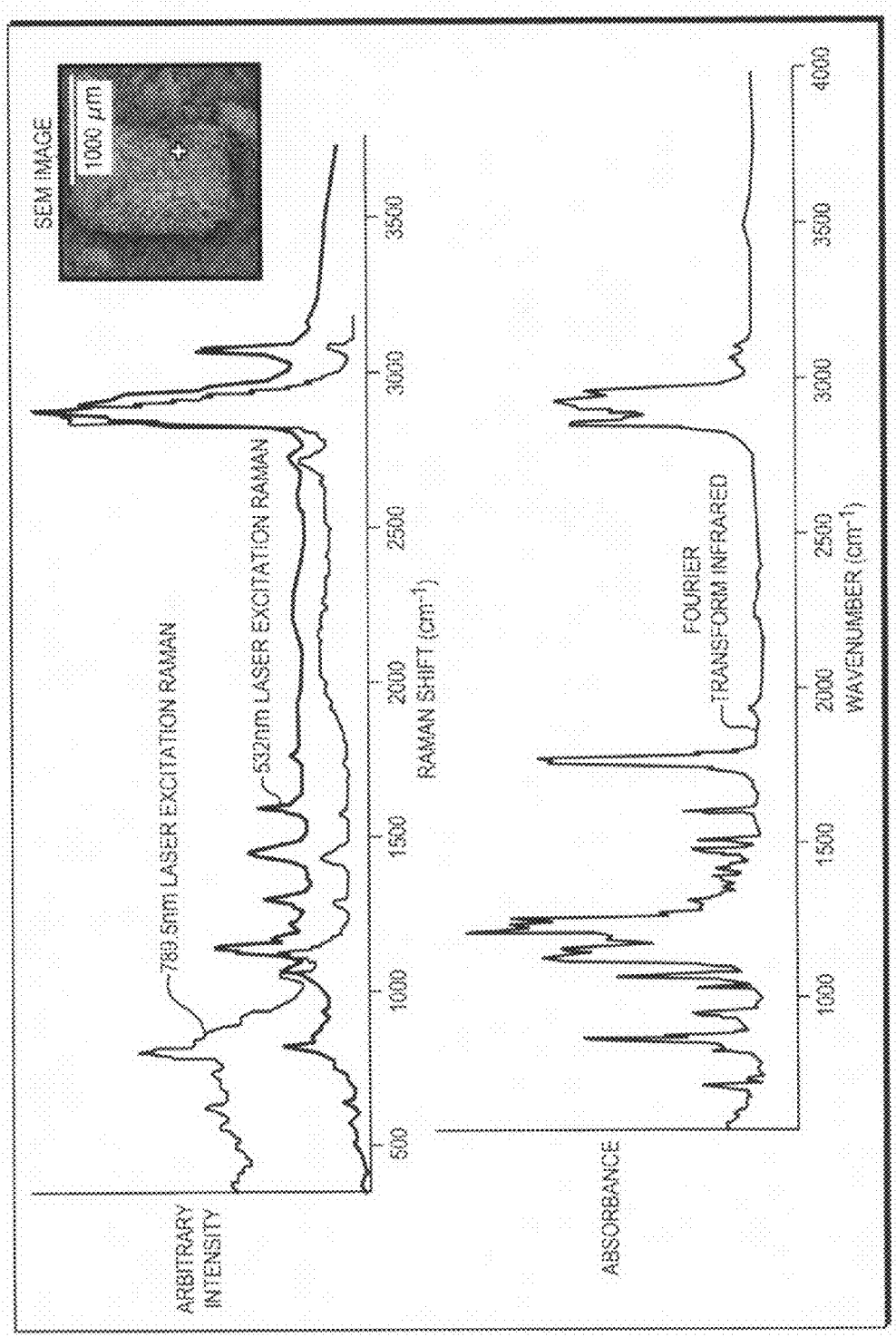
Figure 5N:
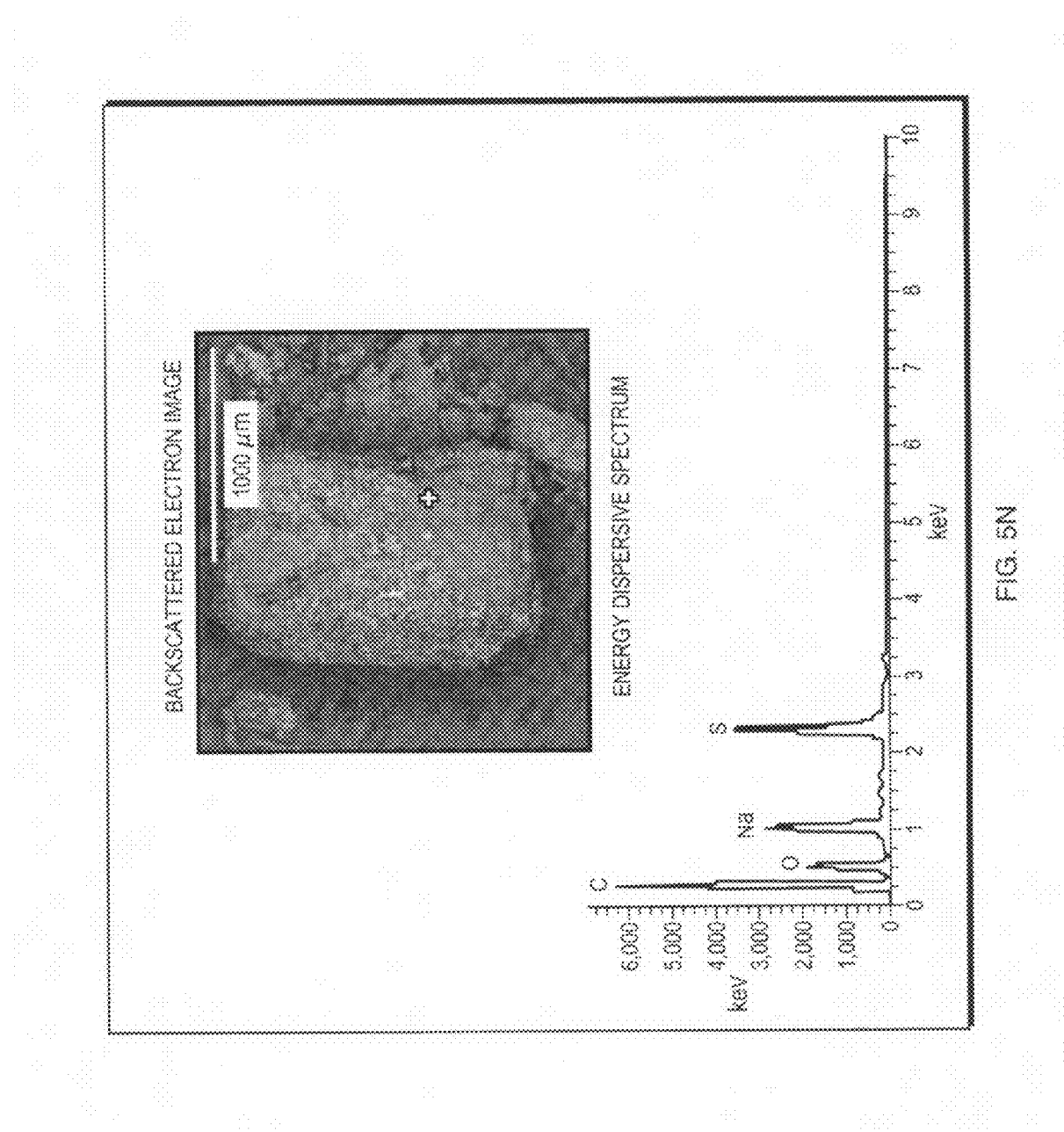
Figure 50:
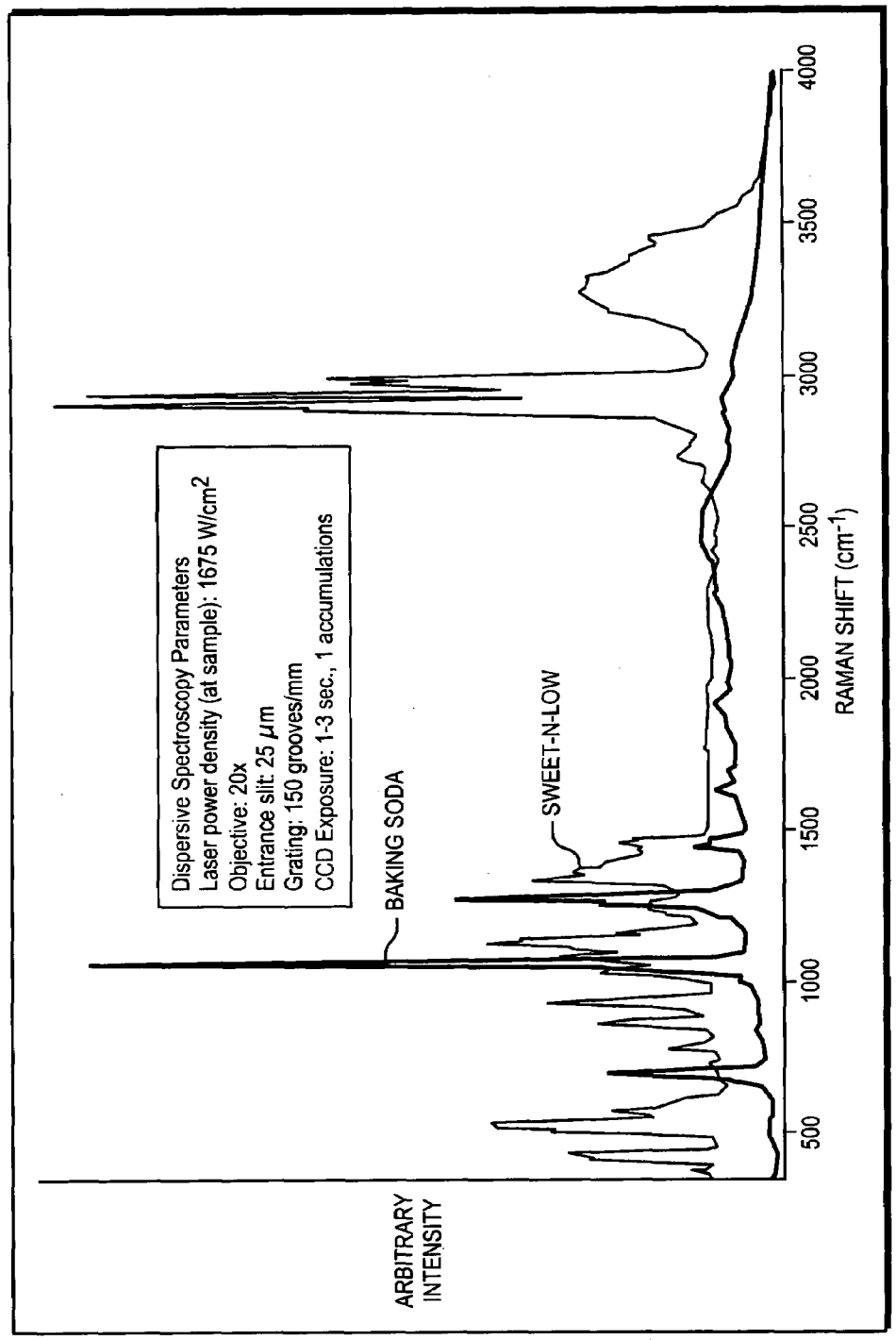
Figure 5P:
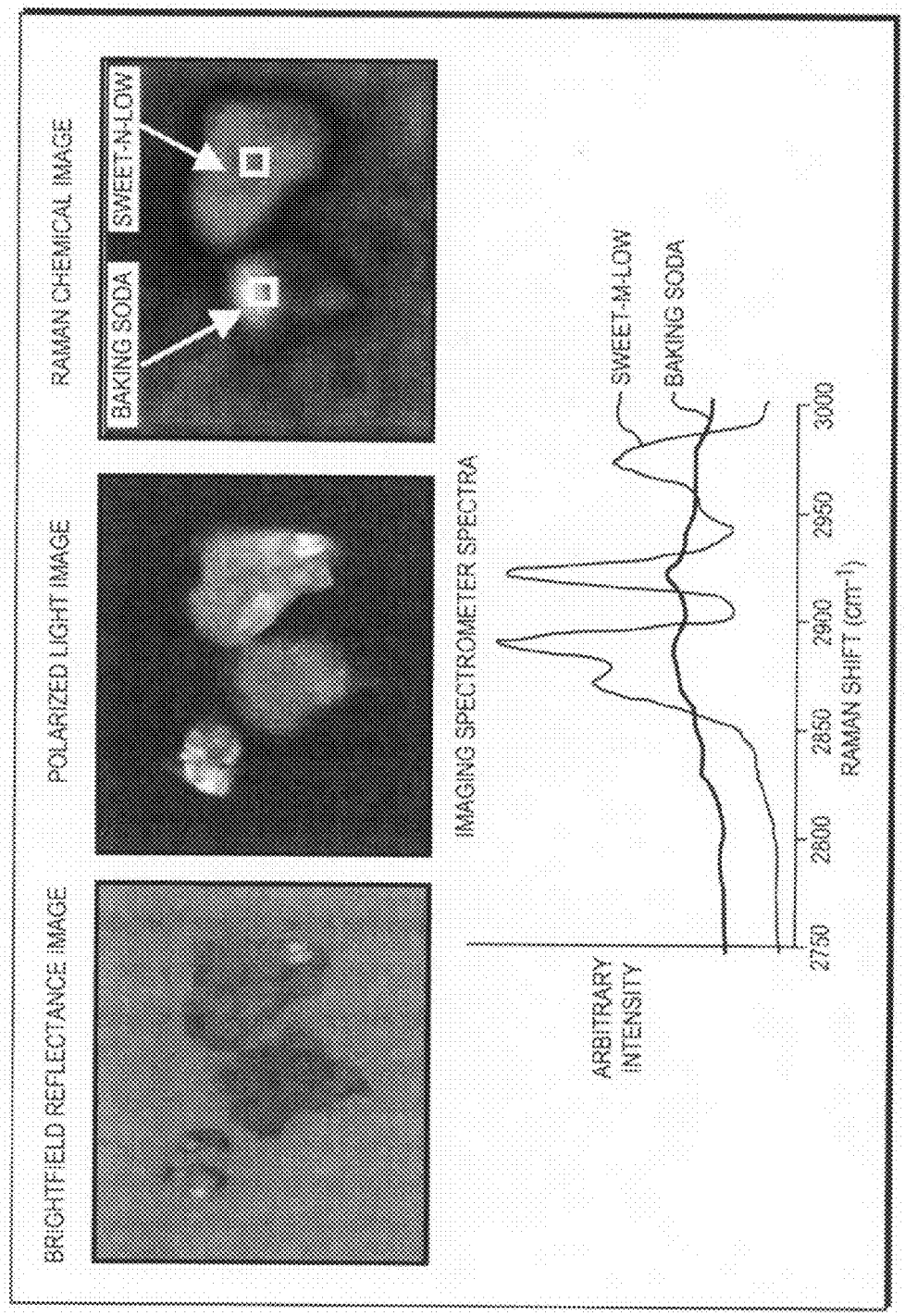
Figure 5Q:
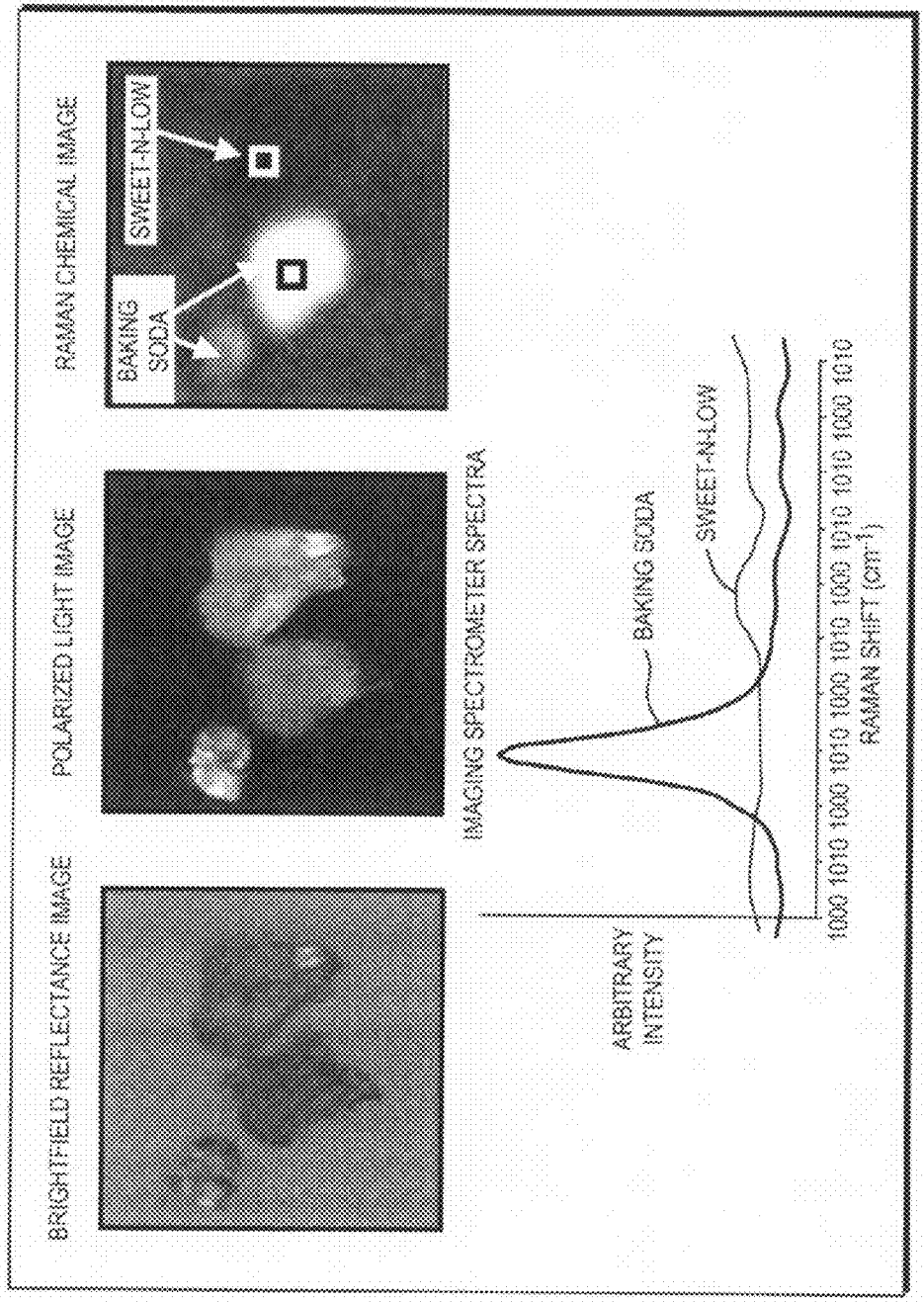
Figure 5R:
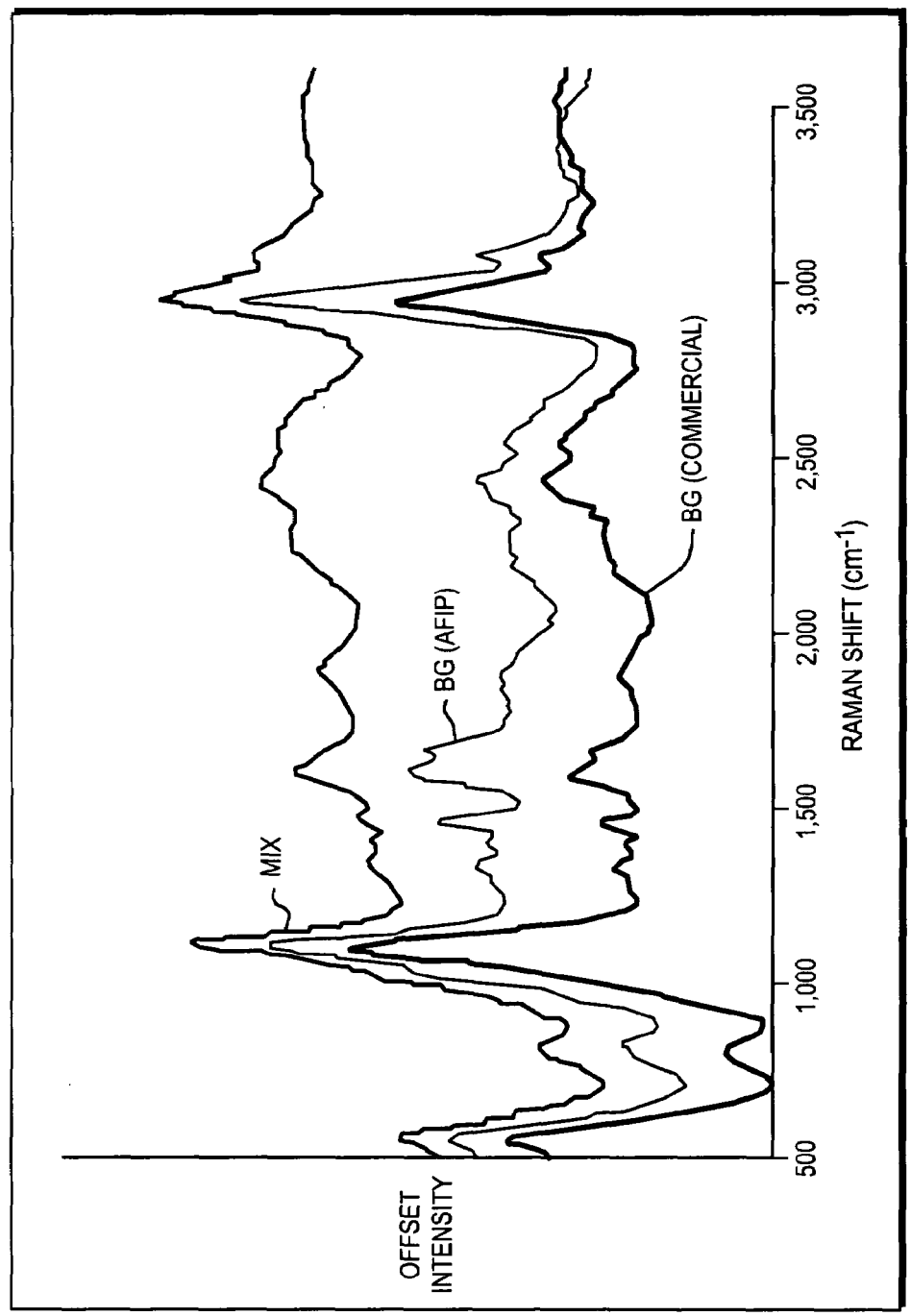
FIG. 5R shows Raman spectra of sample BG spores compared with commercially available BG spores. A Raman spectrum of a mixture of the 2 samples is shown, as well. Raman indicates the samples are similar, almost identical.
Figure 5S:
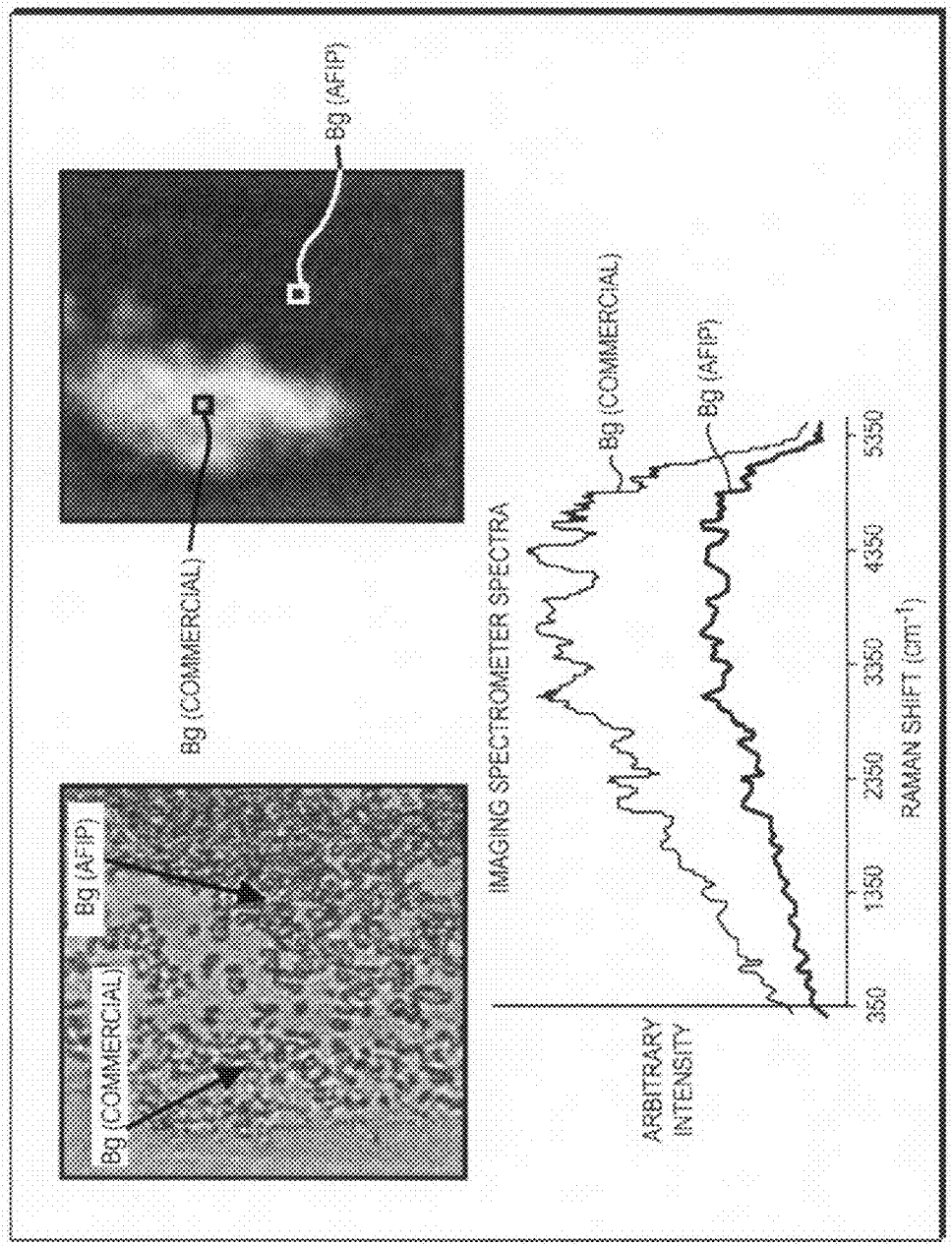
FIG. 5S shows a Chemical Image where the 2 similar spores of *Bacillus subtilis* are differentiated on the basis of autofluorescence differences.
Figure 5T:
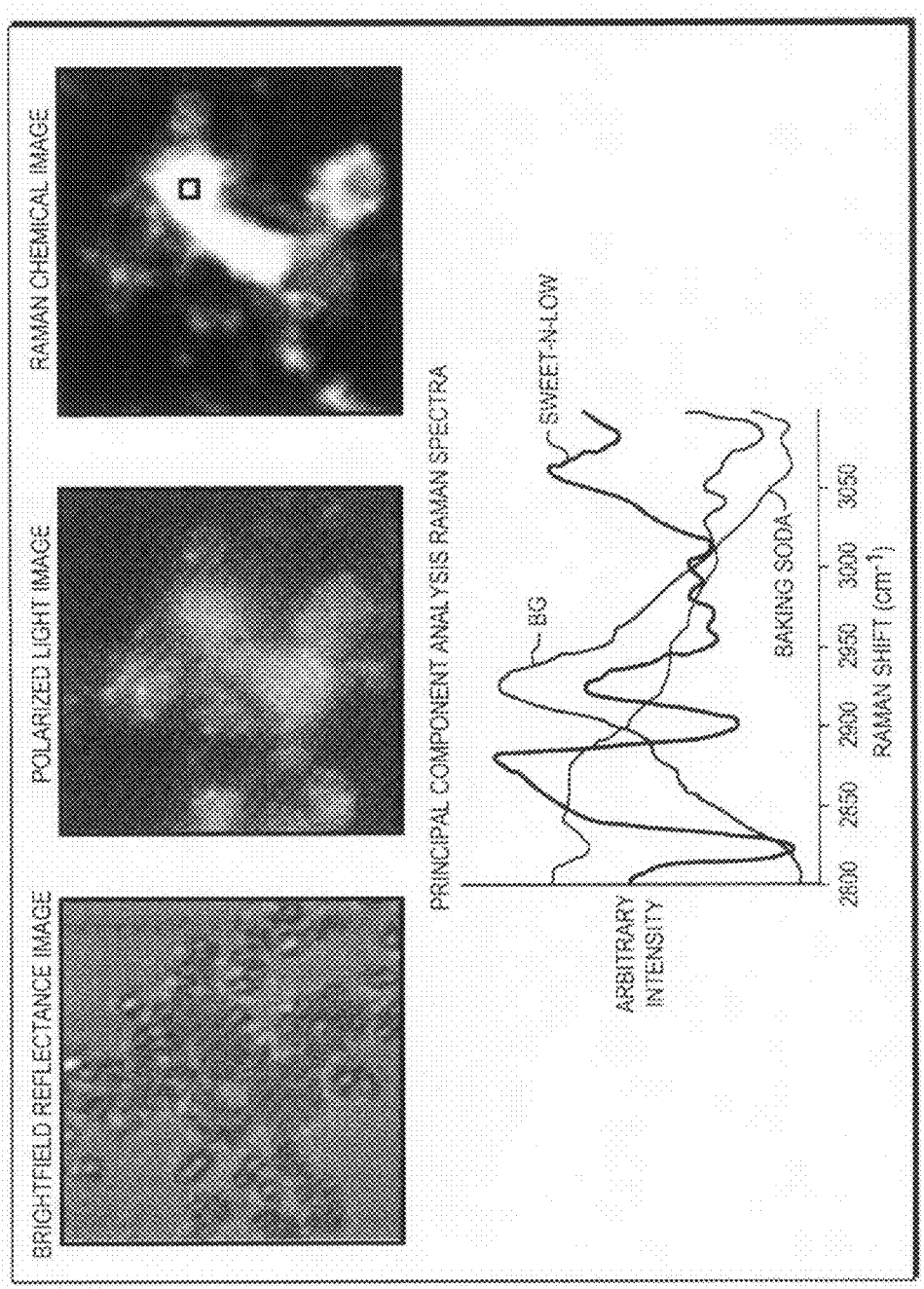
FIG. 5T shows a Raman Chemical Imaging where the 2 powders (Baking Powder and Sweet-n-Low) from FIG. 5O are mixed with BG spores. The 3 species can readily be discriminated.
Figure 5U:
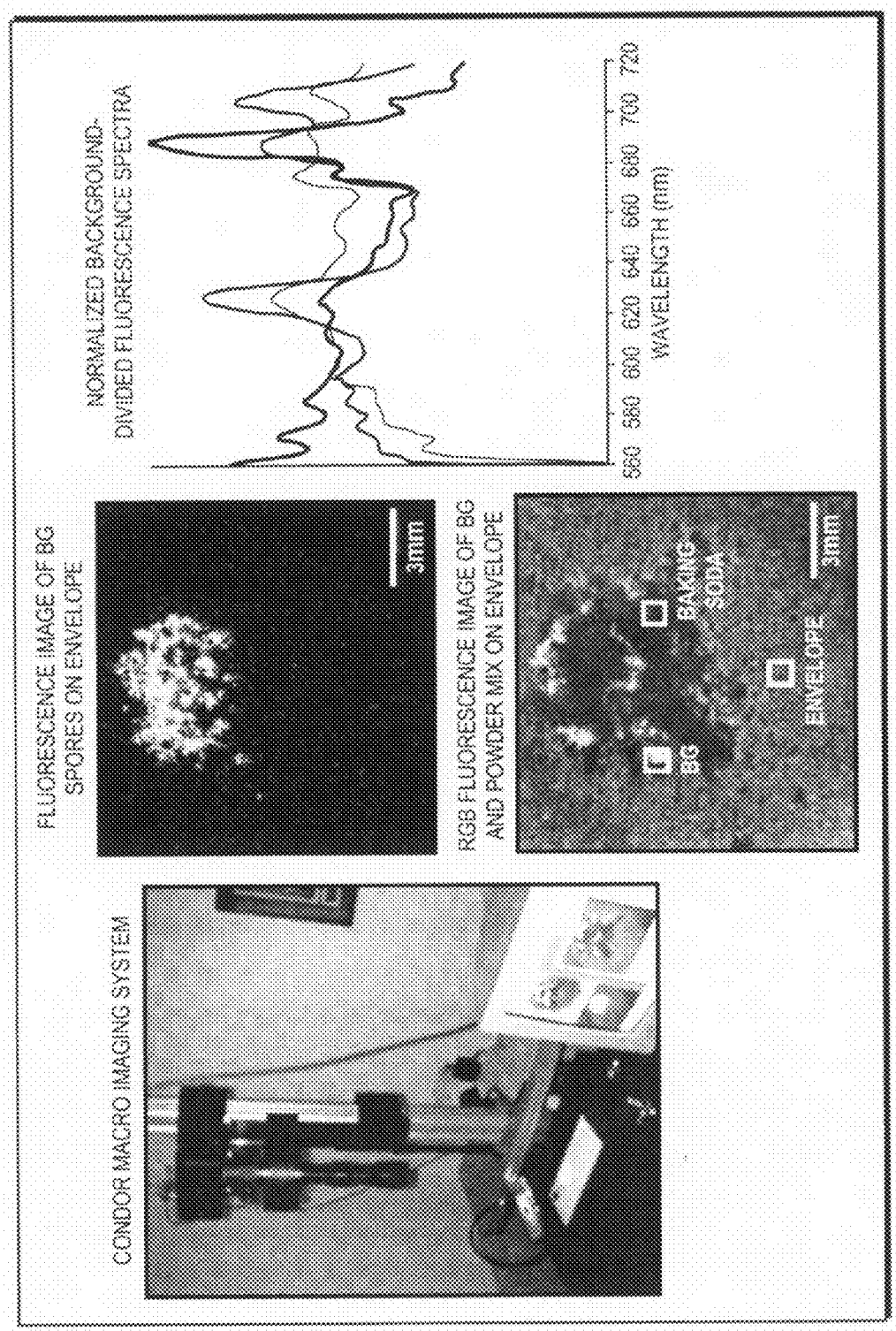
FIG. 5U shows efforts to detect BG in the presence of a white powder (Baking soda) on an envelope.
Figure 5V:
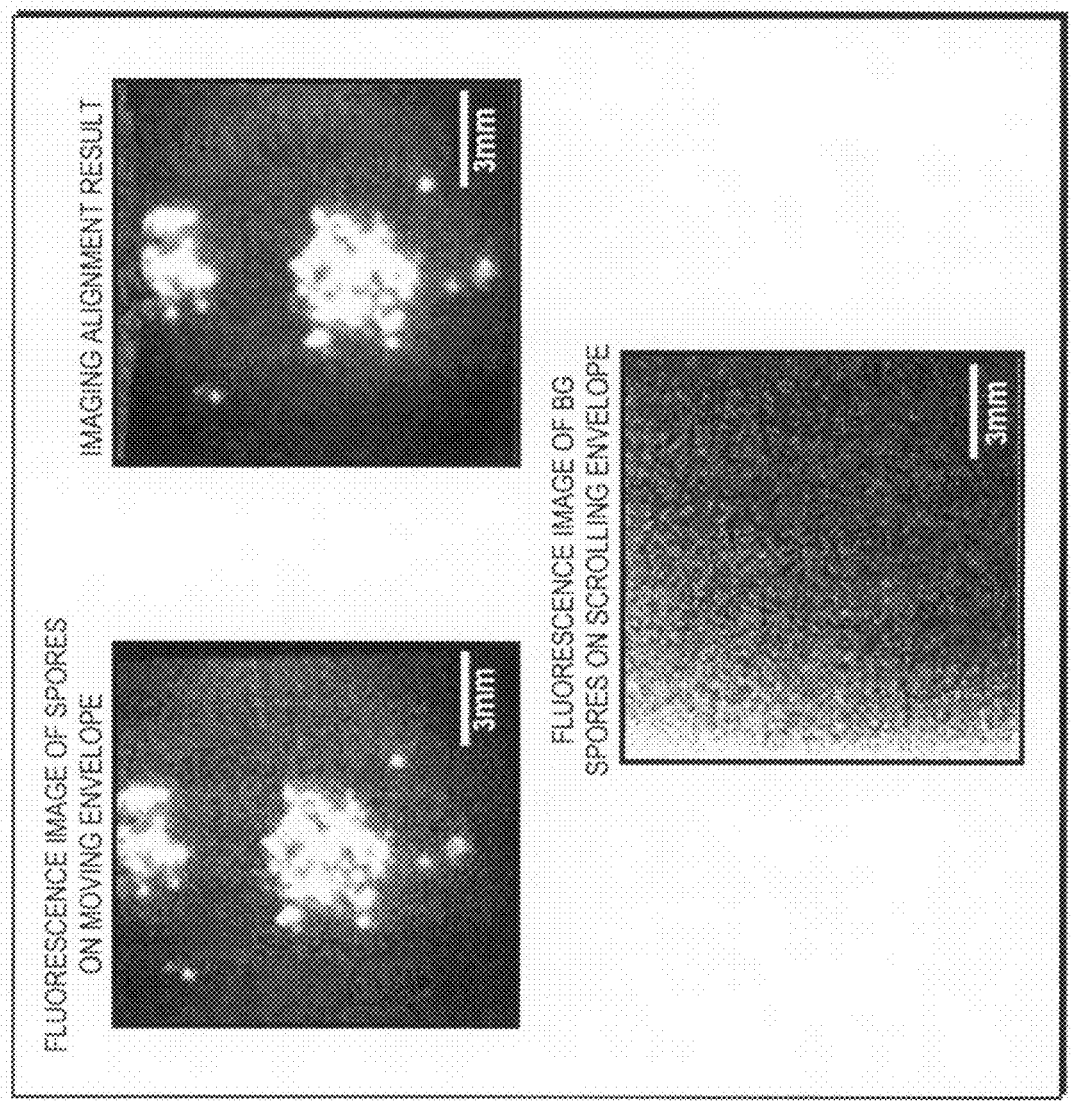
FIG. 5V shows BG on an envelope imaged while the envelope is moving.
Figure 6A:
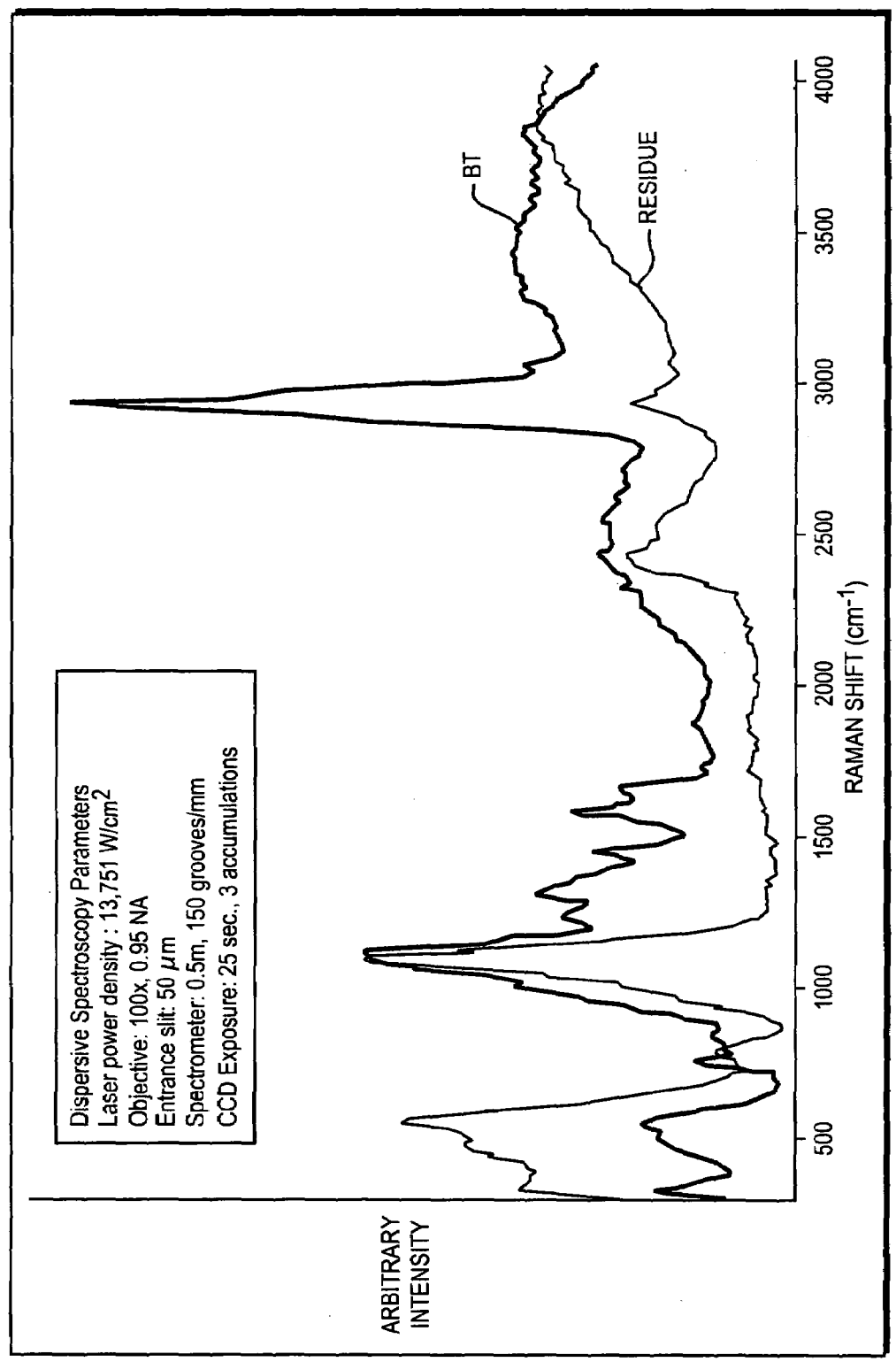
FIGS. 6A-6F show the results from additional spore samples selected specifically because the inherent difficulty in differentiating these species. They include *Bacillus thuriengensis* (BT), *Bacillus cereus* (BC) and BG. The Raman spectra from the 3 spores are different. These differences suggest a FIG. 10 shows Raman Chemical Imaging of actual individual *Bacillus anthracis* (Anthrax) spores as well as additional demonstrations of RCI's power to reproducibly distinguish between similar materials.
Figure 6B:
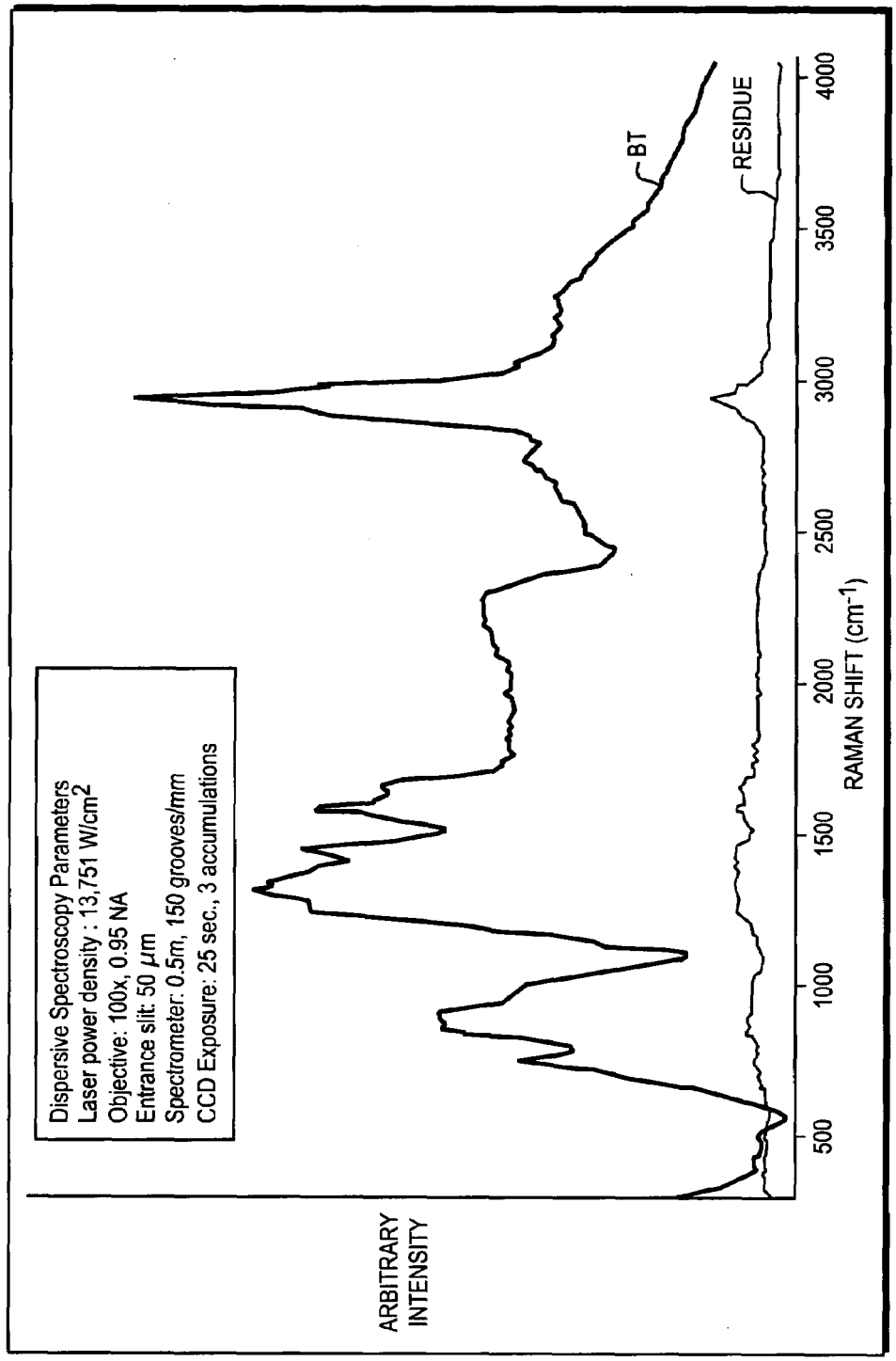
Figure 6C:
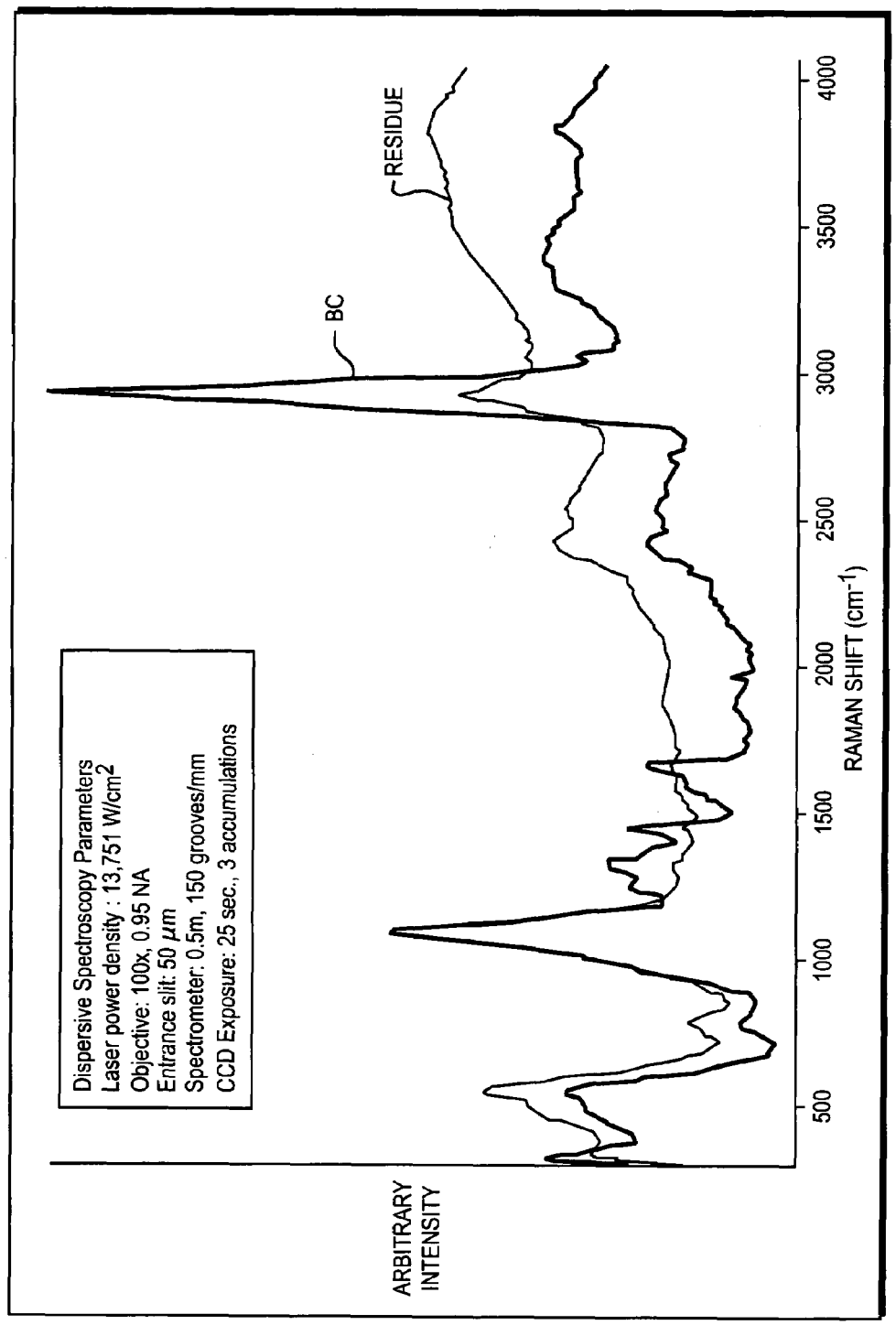
Figure 6D:
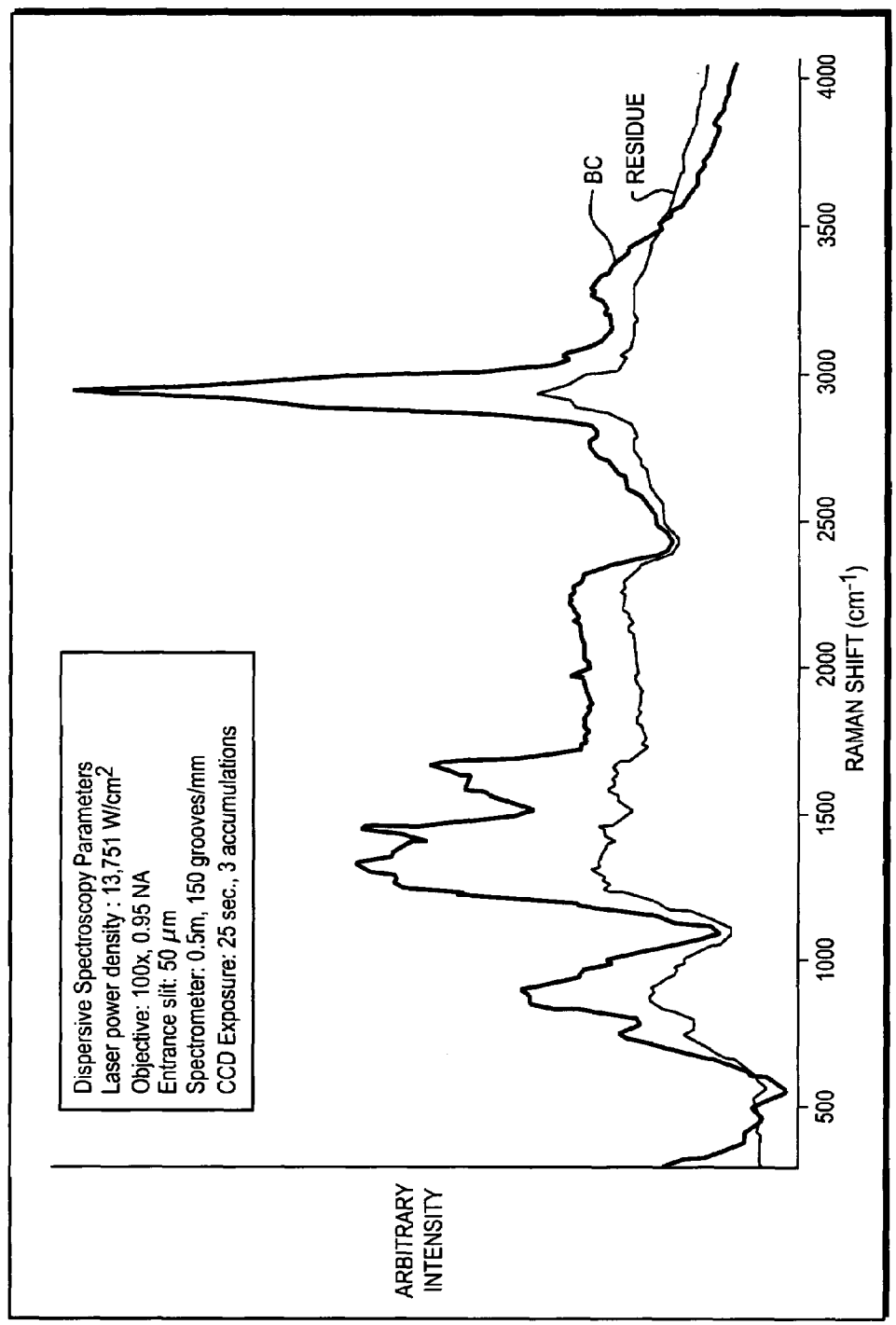
Figure 6E:
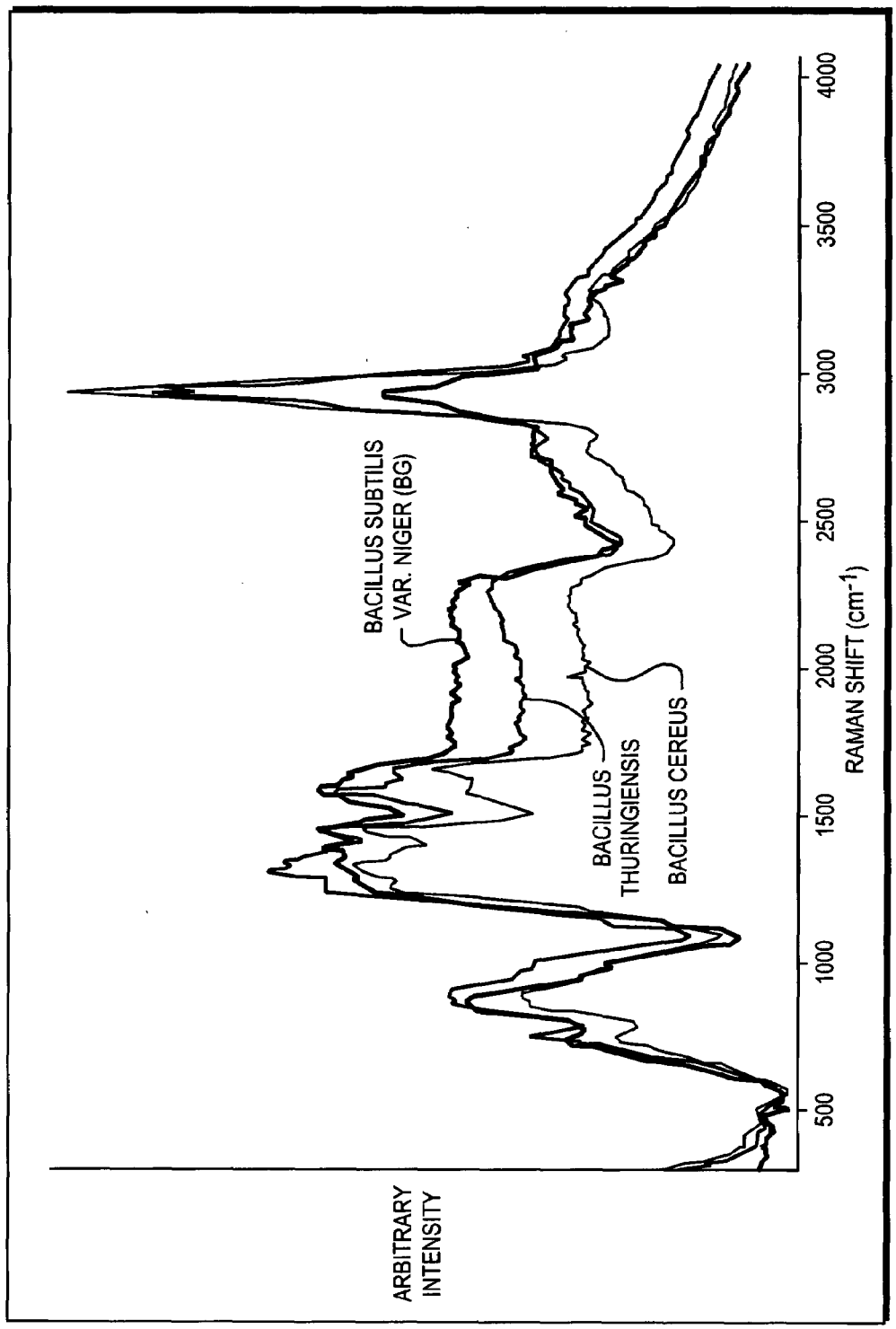
Figure 6F:
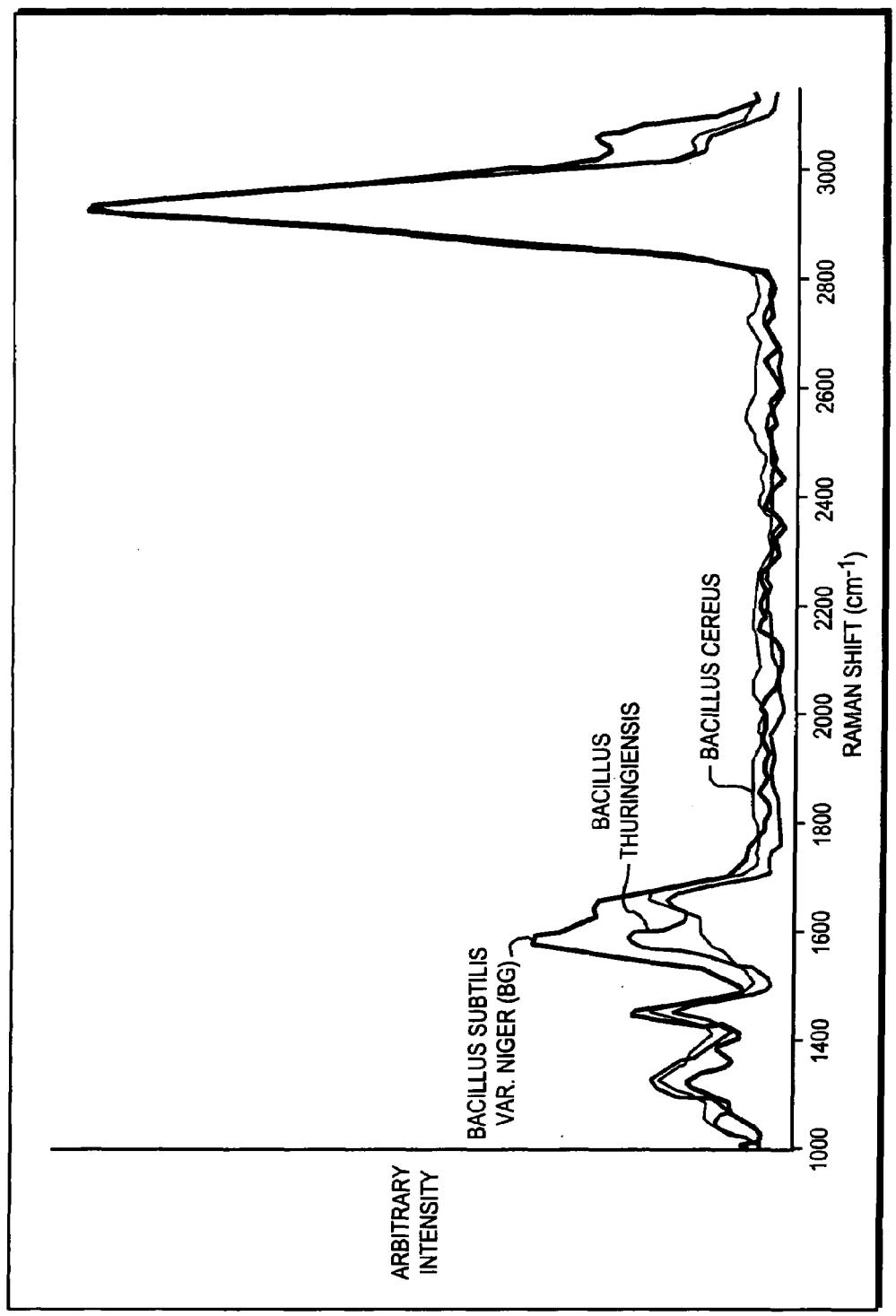
Figure 7:
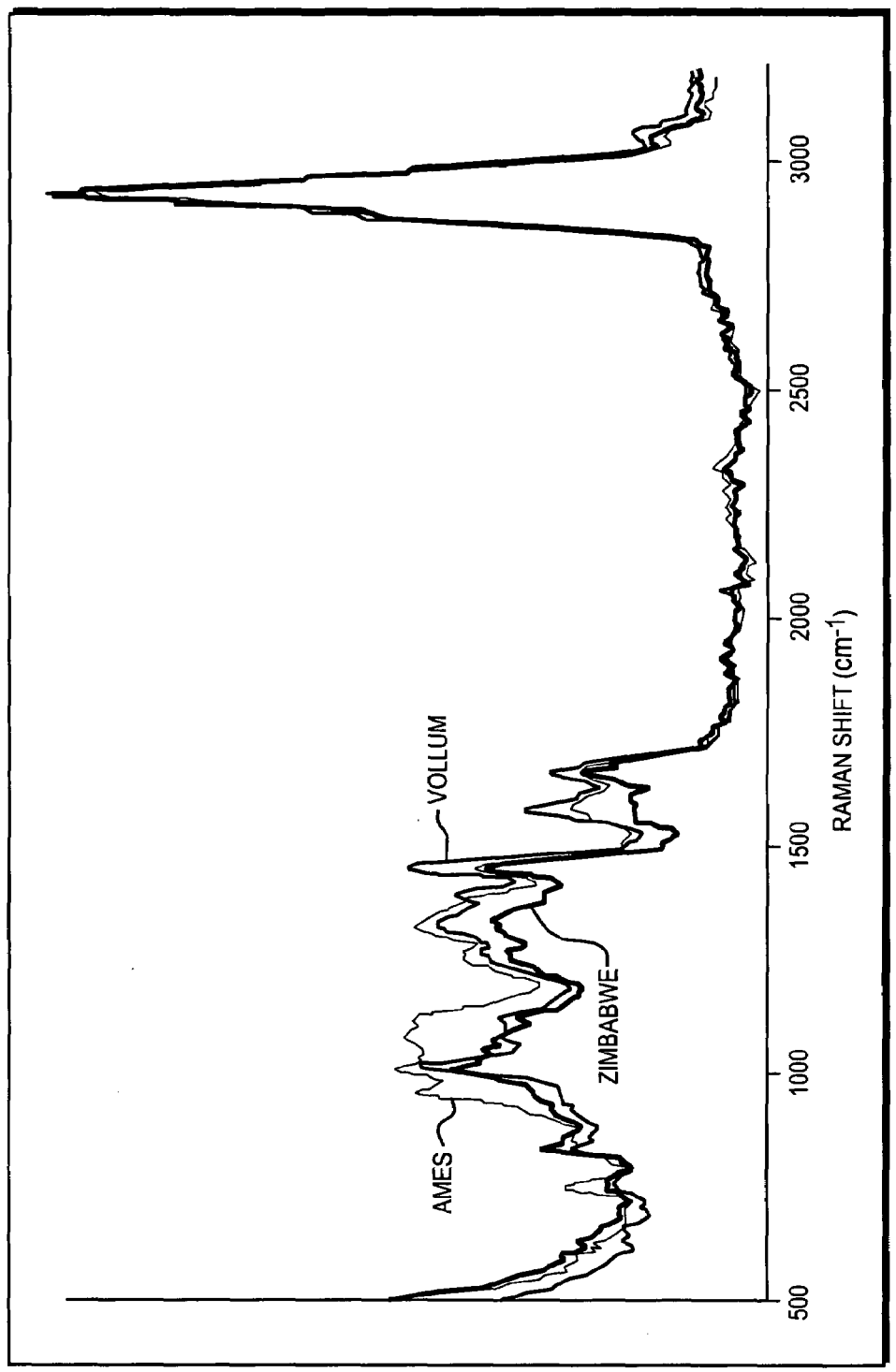
Figure 8:
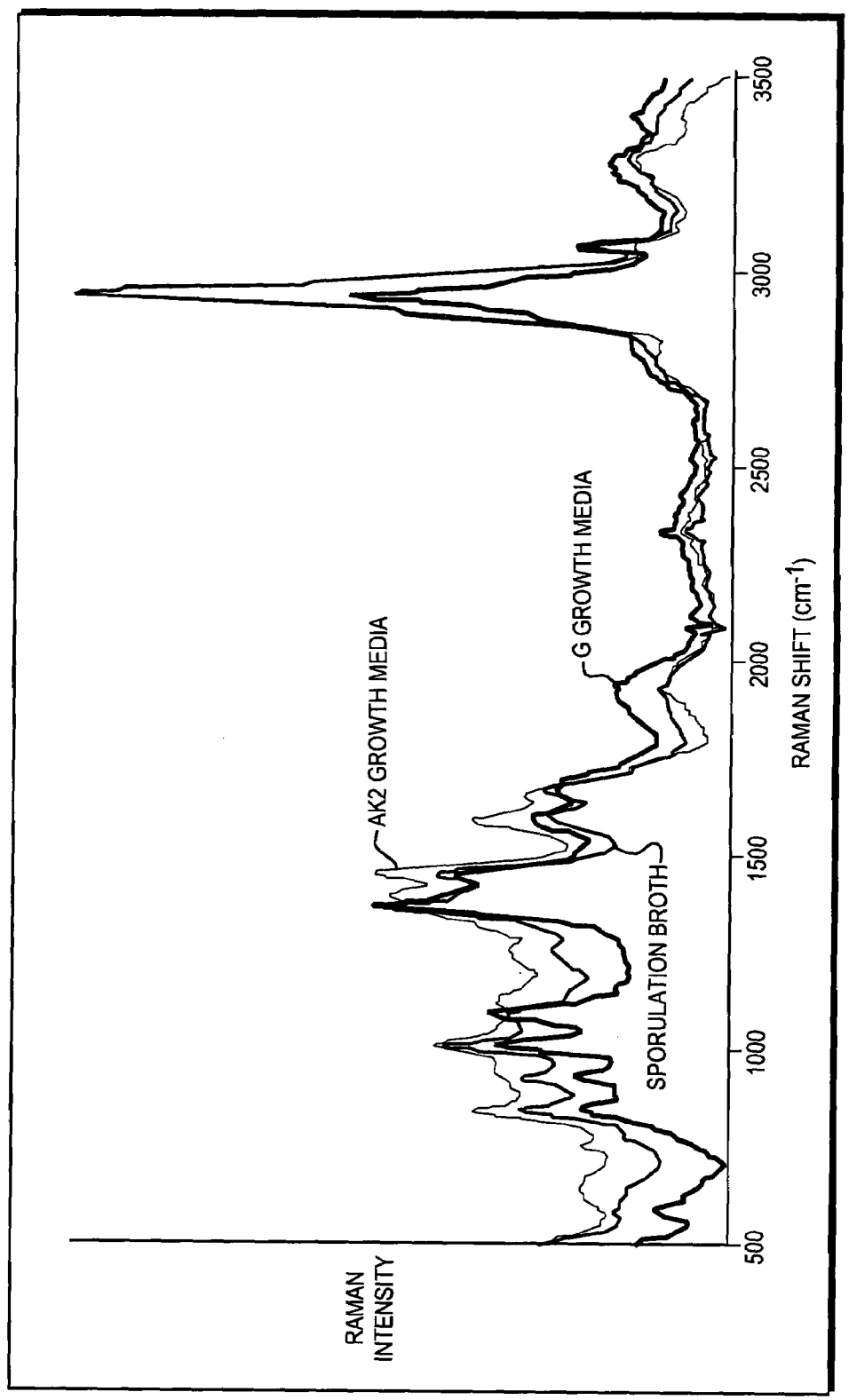
Figure 9:
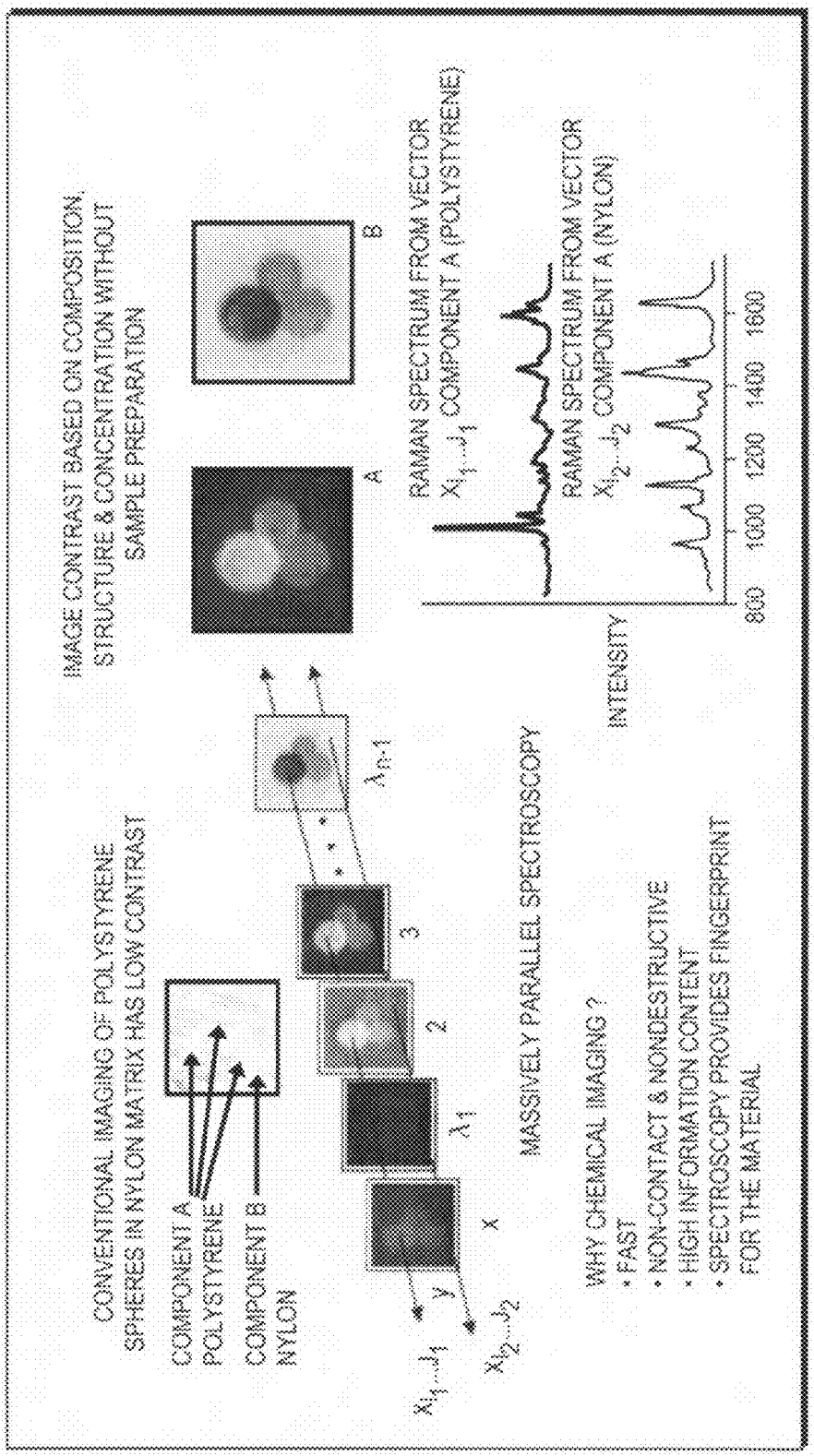
Figure 10:
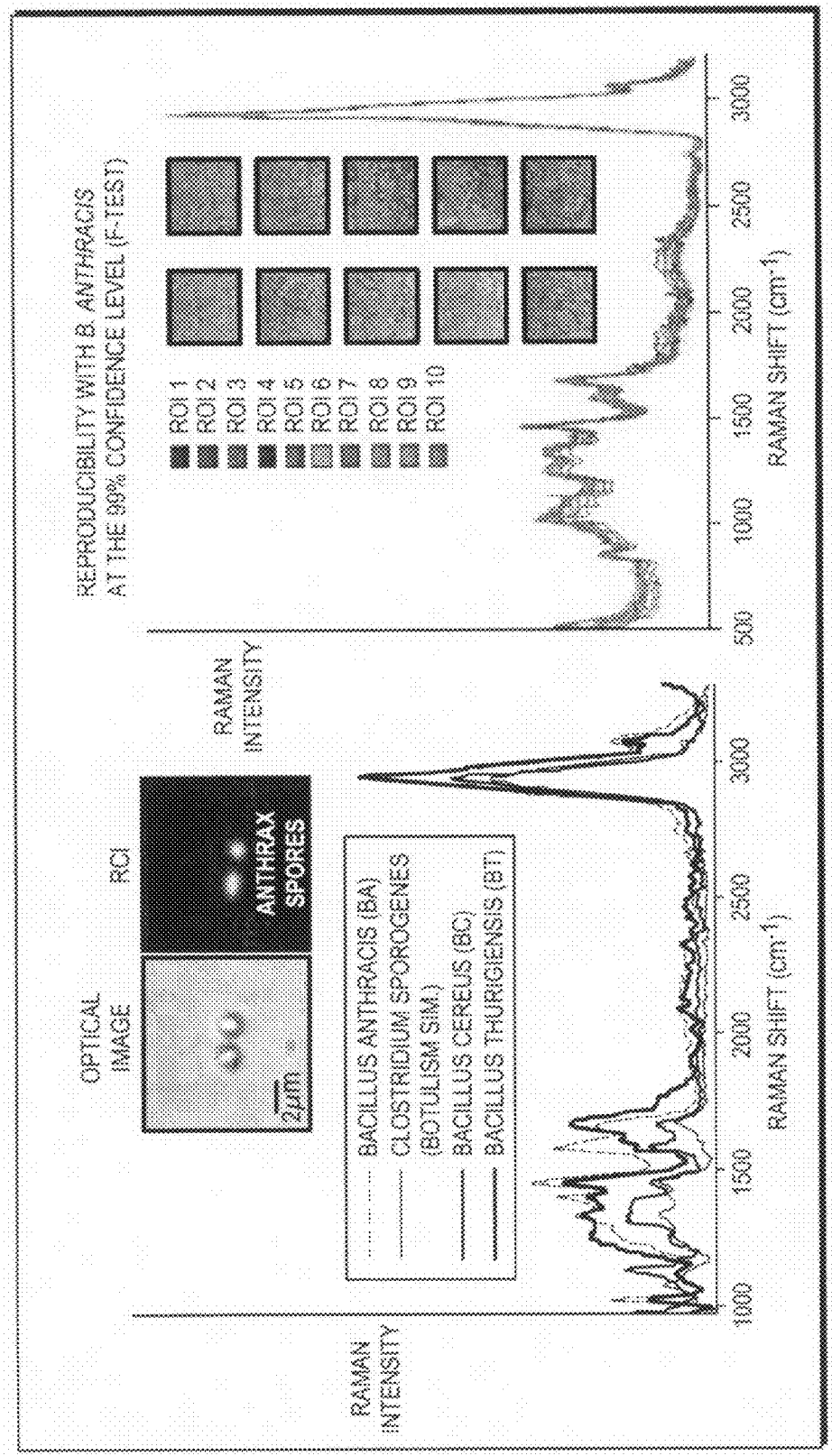
Figure 11:
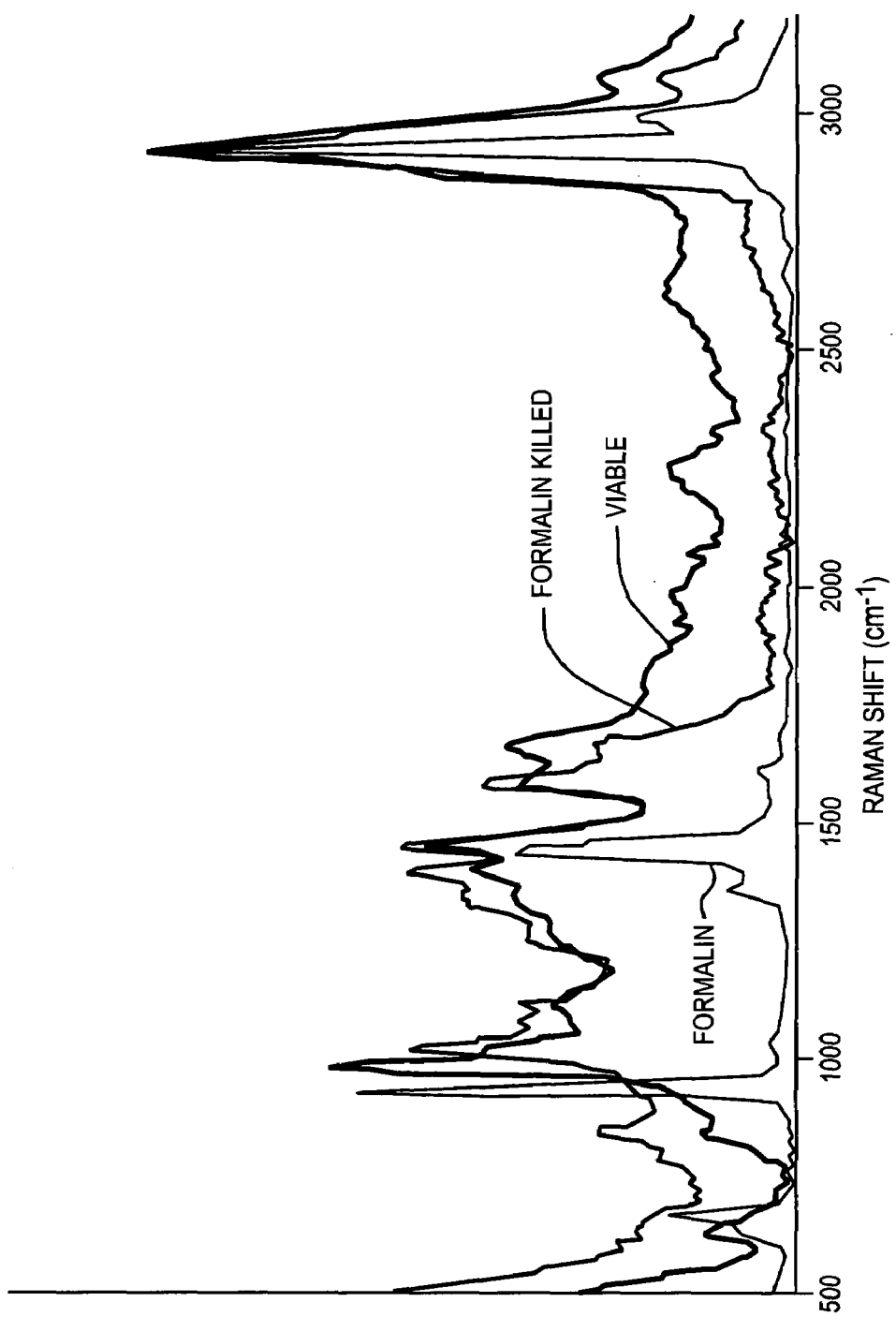
FIG. 11 shows how RCI can be applied to distinguish between viable and non-viable endospores, a critical variable in determining real threat level.

FIGS. 5A-5V show the results of rapid spectroscopic examination of unidentified samples supplied by the US Armed Forces Institute of Pathology (AFIP). These samples include 4 samples comprising 6 unknown powders and a sample of BG spores.

FIG. 5A shows Raman spectra (green laser excitation) of the 6 unidentified powders through the vials.

FIG. 5B shows Raman spectra (red laser excitation) of the 6 unidentified powders.

FIGS. 5C-5D (Sample 1331-002) show Raman, IR and SEM-EDS results on a first of the 6 unidentified powders. The sample is inorganic and most likely talc.

FIGS. 5E-5F (Sample 1325-002) show Raman, IR and SEM-EDS results on a second of the 6 unidentified samples. The sample is organic and most likely starch, possibly corn starch.

FIGS. 5G-5H (Sample 1303-002) show Raman, IR and SEM-EDS results on a third of the 6 unidentified powders. The sample is organic and most likely starch, possibly corn starch.

FIGS. 5I-5N (Sample 1291-006) show Raman, IR and SEM-EDS results on the remaining unidentified powders. There are 3 distinct types of powders in this sample. All 3 have organic content, while 2 of the 3 are fairly rich in aluminosilicates. One of the powders is likely a complex aromatic hydrocarbon.

FIGS. 5O-5Q show Raman spectra and images of 2 common white powders that can easily be differentiated with Raman Chemical Imaging.

FIG. 5R shows Raman spectra of sample BG spores compared with commercially available BG spores. A Raman spectrum of a mixture of the 2 samples is shown, as well. Raman indicates the samples are similar, almost identical.

FIG. 5S shows a Chemical Imaging where the 2 similar spores are differentiated on the basis of autofluorescence differences.

FIG. 5T shows a Ranan Chemical Imaging where the 2 powders from FIG. 5O are mixed with BG(AFIP). The 3 species can readily be discriminated.

FIG. 5U shows efforts to detect BG in the presence of a white powder (Baking soda) on an envelope.

FIG. 5V shows BG on an envelope imaged while the envelope is moving.

FIGS. 6A-6F show the results from additional spore samples selected specifically because the inherent difficulty in differentiating these species. They include *Bacillus thuriengensis* (BT), *Bacillus cereus* (BC) and BG. The Raman spectra from the 3 spores are different. These differences suggest a good chance of differentiating anthrax from non-threats. The details follow:

FIG. 6A shows raw Raman spectra of BT and the suspension residue. The residue is from the suspension liquid.

FIG. 6B shows background corrected spectra of BT and residue. Both the spores spectrum and residue spectrum have been divided by a spectrum of the microscope slide.

FIG. 6C shows raw Raman spectra of BC and the suspension residue.

FIG. 6D shows background corrected spectra of BC and residue.

FIG. 6E shows a compilation of sample BT, BC and BG spectra with microscope slide background correction. The spectra are different. The differences are greatest in the fingerprint region.

FIG. 6F shows a compilation of the 3 spores after baseline subtraction and normalization to the CH region spectral feature (~2950 $cm^{-1}$).

FIG. 7 shows how RCI can be applied to distinguish between multiple bacterial strains within a single species.

FIG. 8 shows how RCI can be applied to distinguish between the same species and strain of bacteria grown under differing conditions.

FIG. 9 shows a schematic description of RCI.

FIG. 10 shows Raman Chemical Imaging of actual individual *Bacillus anthracis* (Anthrax) spores as well as additional demonstrations of RCI's power to reproducibly distinguish between similar materials.

FIG. 11 shows how RCI can be applied to distinguish between viable and non-viable endospores, a critical variable in determining real threat level.

Anthrax spores have been Raman imaged in a secure biohazard laboratory (FIG. 10). Different strains of Anthrax spores have been differentiated by Raman Imaging (FIG. 7). Additionally, Raman Chemical Imaging has been used to differentiate same species and strain grown under different environmental conditions and/or growth medium (FIG. 8). This ability can have useful investigatory applications. And, RCI has been used to differentiate viable from non-viable endospores (FIG. 11). Viability of suspect spores is a critical variable in determing the real threat posed. The inventors anticipate that the following pathogenic microorganisms will be susceptible to detection and classification as to species, strains, and viability by the Raman spectral profile and Raman imaging: protozoa; cryptosporidia; *Escherichia coli*; Plague (*Yersinia pestis*; Smallpox (*variola major*); Tularemia (*Francisella tularensis*; Brucellosis (*Brucella* species; *Clostridium pertringens*; Glanders (*Burkholderia mallei*; Melioidosis (*Burkholderia pseudomallei*; Psittacosis (*Chlamydia psittaci*; Q fever (*Coxiella burnetii*; Typhus fever (*Rickettsia prowazekii; Vibrio; Giardia; Candida albicans; Enterococcus faecalis; Staphylococcus epidermidis; Staphylococcus aureus; Enterobacter aerogenes; Corynebacterium diphtheriae; Pseudomonas aeruginosa; Acinetobacter calcoaceticus; Klebsiella pneumoniae; Serratia marcescens*; filoviruses (such as Ebola and Marburg viruses), naviruses (such as Lassa fever and Machupo viruses) and alphaviruses (such as Venezuelan equine encephalitis, eastern equine encephalitis, and western equine encephalitis). The pathogenic microorganism may further comprise the following bacteria: *S. aureus, E. coli*, CoNS, *Enterococcus* spp., *Klebsiella* spp. *S. pneumoniae, P. aeruginosa, Enterobacter* spp, *Beta-hemolytic streptococci; P. mirabilis*, Viridans group streptococci, *Acinetobacter* spp, *Serratia* spp., *Citrobacter* spp., *S. maltophilia, P. agglomerans, Salmonella*, spp., *Haemophilus* spp., *M. morganii*, and *Corynebacterium* spp. The pathogenic microorganism may yet further comprise the following fungi: *Microsporum audouini, Microspotum canis, Microsporum gypseum, Trichophyton mentagrophytes* var. *mentagrophytes, Trichophyton mentagrophytes* var. *interdigitale, Trichophyton rubrum, Trichophyton tonsurans, Trichophyton verrucosum*, and *Epidermophytum floccosum.*

The inventors further anticipate that a variety of spectroscopic and imaging modalities may be used to detect and classify as to species, strains, and viability of these pathogenic microorganisms and biological agents. The spectroscopic and imaging modalities include one or more of the following: Raman spectral profile and Raman imaging; fluorescence spectral profile and fluorescence imaging; near infrared spectral profile and near infrared imaging; and mid-infrared spectral profile and mid-infrared imaging.

Advanced image analysis and chronometric tools take these differences in fluorescence spectra and perform a spatial identification of species, producing the image in FIG. 4. The following is a representative algorithm for performing this analysis:

1) Divide the raw image by a background image (taken without the sample).

2) Do cosmic filtering on the resultant image (median filtering for pixels whose value differs significantly from the mean of a local neighborhood).

3) Use an alignment procedure to correct for slight movements of the sample during data collection.

4) Apply a spatial average filter.

5) Perform a spectral normalization (helps correct for varying illumination across the sample).

6) Perform a spectral running average over each set of three spectral points.

7) Extract a set of frames corresponding to 550 to 620 nm. The spectra for both bacterial spores (*Bacillus subtilis* var *niger* and *Bacillus pumilus*) are essentially linear over this range. *Bacillus sublilis* var *niger* has a positive slope and *Bacillus pumilus* has a negative slope.

8) Create a single frame image in which each intensity value is the slope of the spectral sub-region (from the last image). The slope is determined via a least-squares fit.

9) Scale the resulting image between 0 and 4095. Keep track of the point from 0 to 4095 that corresponds to 0 in the prior image (the "Zero point").

10) Create a mask image from a series of steps: a) From the aligned image (3$^{rd}$ step), calculate a single frame "brightest" image in which the intensity of each pixel is the maximum intensity value for each spectrum. b) Scale this brightest image between 0 and 4095. c) Create a binarized image from the scaled image, in which every pixel whose intensity is greater than 900 is set to 1 in the new image and every pixel whose intensity is less than 900 is set to 0 in the new image. The value of 900 was chosen by an examination of the histogram associated with the scaled image. A future improvement to the algorithm would be to automatically select the threshold by numerically analyzing the histogram for a given image.

11) Multiply the scaled image from step 9 by the mask image from step 10. This restricts the visual display to only areas that correspond to spores. The result is a gray scale image in which intensity values below the zero point defined in step 9 correspond to *Bacillus pumilus* and the intensity values above the zero point correspond to *Bacillus subtilis* var *niger*.

12) The final RGB image is then created by setting all the "negative" values to red and all the "positive" values to green.

Applications

There is a great need for a spectroscopic imaging instrument that can provide high throughput, non-contact, real-time detection, classification and identification of BWAs and CWAs with high accuracy and with limited or no sample preparation required. The user base for an instrument suitable for objective assessment of BWAs and CWAs will consist of hazardous materials (HAZMAT) teams, government and private facilities where potential threats are high, mail handling facilities, academic, industrial and medical research laboratories, etc.

The benefits to the target users of an instantaneous Anthrax or other microoganism threat detection system will be substantial. Configured in the macroscopic version of the technology, spectroscopic imaging can be employed for rapid assessment of large areas for suspect BWAs and CWAs based on their fluorescence, NIR and/or UV/visible response. Configured in the microscopic mode, positive detection, classification, identification and visualization of suspect BWAs and CWAs can be made. Configured in the endoscopic mode, BWAs and CWAs can be detected, classified, identified and visualized remotely. Configured in FAST mode, BWAs and CWAs can be detected, classified, identified and visualized remotely or at the microscope in real-time. When configured as an air sampler, unambiguous detection of BWAs and CWAs can be done.

When performed in combination the effectiveness of characterizing BWAs and CWAs will likely be enhanced. Benefits will include, but are not limited to, the following:

Rapid large area scanning to detect suspect BWAs and CWAS.

Positive detection, classification, identification and visualization of suspect BWAs and CWAs.

Non-contact.

Limited or no sample preparation required.

Remote detection, classification, identification and visualization of suspect BWAs and CWAs.

Real-time detection, classification, identification and visualization of suspect BWAs and CWAs in solid or gaseous samples.

Specific applications of a spectroscopic imaging system for instantaneous Anthrax detection will include the following:

Discrimination of threatening and non-threatening 'masking' agents.

Spatial distribution of BWAs and CWAs.

Spatial distribution of BWAs and CWAs down to single bacterial spores.

Advantages Over Currently Available Technology.

Traditional approaches to detection of BWAs and CWAs include inoculation methods, enzyme-linked immunosorbent assay (ELISA) methods, BioThreat Alert (BTA) test strips, DNA-based tests, DNA chip analyses and mass spectrometry. Inoculation methods involve the inoculation of suspect culture or specimen into an animal that is then observed for development of disease. In addition to animal cruelty issues, there are drawbacks with this approach including the extensive amount of time required to reach a point of detection.

ELISA tests involve antibody detection. This technique is also slow and suffers from high false positive (unrelated antibody reacts with antigen nonspecifically) and worse, high false negatives (interfering compounds present in blood or antibodies not concentrated enough to be detected). Furthermore, a patient can test positive to antibodies long after the patient has recovered.

BTA test strips are small plastic devices that work very much like a home pregnancy test. The test strips contain specific antibodies that change color on the strip indicating the presence of a bio-threat agent. A negative result means the bio-threat agent is not present within the detection limit of the strip. Although results can be obtained in a relatively short period (15 minutes), the incidence of false negatives and false positives is high.

DNA-based tests detect agents by recognizing their genetic sequences. While more sensitive than BTA test strips, DNA-based tests are susceptible to masking agents and involve a lengthy analysis time. DNA chip analysis involves the immobilization of DNA strands on a Si or glass wafer chip. DNA will bind to or hybridize complementary DNA strands in the sample being tested. A specially designed microscope detects where the DNA hybridize. Amplification is achieved by polymnerase chain reaction (PCR). Detection of bio-threat agent is reported to be possible within minutes.

The limitations of DNA-based methods are two-fold. First, DNA methods are designed to detect a specific bio-threat agent through its unique DNA sequences. Therefore, each DNA test is specific to one agent and if it is desired to detect additional agents, additional test reagents must be developed. A second limitation revolves to the problems of false negatives and false positives due to environmental contamination. DNA tests are well known to have problems yielding correct results in "real-world" samples.

Mass Spectrometry (MS) uses the pattern of mass fragments when a cell or spore is subjected to an ionization process under high vacuum to characterize organisms. It has the advantage of very sensitive detection but requires a sophisticated sampling system in order to deliver a representative sample to the ionizer. The main limitation of MS is that it requires the use of high vacuum pumps that are inherently delicate and expensive. An additional limitation is that it is a destructive technique, in contrast to Spectroscopic Chemical Imaging, which is a completely no-destructive technique.

Alternative technologies/opportunities include probes or microscopes based on spectroscopic methods including Raman, fluorescence, NIR, etc. for rapid, non-contact and accurate detection of BWAs and CWAs. These types of tools offer the potential to detect, classify, identify and visualize the distribution of BWAs and CWAs in the presence of other. BWAs, CWAs and/or non-threatening 'masking agents in either a local or remote environment characteristics that no traditional method can provide. Such tools would greatly reduce the incidence of false positives and false negatives and would provide a way to determine if a true bio-threat exists in minutes.

State-Of-The-Art Spectroscopic Imaging Techniques

Several spectroscopic imaging technologies have evolved that compete with widefield tunable filter-based spectroscopic imaging and FAST technology. These techniques include point scanning, line imaging, spectroscopic imaging using interference filters, Fourier-transform interferometry and Hadamard-transform scanning.

Point scanning involves taking a complete spectrum for a single X,Y position of a sample followed by raster-scanning the sample for the remaining X,Y positions. This method offers advantages of high spectral resolution and full spectral resolution, but lacks high image definition capabilities and is extremely time consuming. Line imaging involves collecting data from vertical sections of the sample characterized by a single value of X and all values of Y, followed by subsequent scanning in the X direction. This method has the nearly the same advantages and disadvantages as the point scanning approach, but can be done more rapidly. Field curvature artifacts are a consequence of line imaging which degrade image quality. The use of single or multiple interference filters can be used to produce a wavelength specific image(s). This method is rapid, cheap and produces high definition images, but lacks spectral resolution and is susceptible to image artifacts.

Fourier-transform interferometers use a mechanically driven interferometer with a CCD-based detection system. Interferograms are imaged with the CCD for subsequent spectral interpretation for each step of the interferometer. This method boasts good spatial resolution but suffers from poor spectral resolution (~100 $cm^{-1}$).

Hadamard transform chemical imaging techniques couple Hadamard mask spatial multiplexing with CCD-based detection to obtain two spatial and one spectral dimension of data. This method offers S/N advantages for low-light level applications such as Raman spectroscopy in addition to sub-nanometer spectral resolution. However, the technique suffers from fair spatial resolution and poor temporal resolution since the latter involves scanning through numerous coding masks.

The ideal chemical imaging system for characterization would provide fast acquisition times (seconds), high spatial resolution (sub-micron) and good spectral resolution (<200 nm). To date, ChemImage's FALCON™ microscope is the only spectroscopic imaging system that meets these requirements.

Other Spectroscopy-Based Imaging Methods

Spectroscopic technologies that compete with those previously mentioned including infrared (IR) spectroscopy are not of great concern based on the resolution needed to see individual BWAs and/or CWAs on the order of 250 microns. IR spectroscopy cannot compete due to the difficulty with water absorption in the IR. Typically, BWAs do not image well because of their aqueous nature. The liquid crystal imaging spectrometer chosen for the spectroscopic imaging systems described here surpasses any dispersive grating or acousto-optic tunable filter (AOTF) technology on the market. The spectral bandpass capability of the LCTF is 8 $cm^{-1}$ allowing for the most effective means to obtain image detail.

Obviously, many modifications and variations of the present invention are possible in light of the above teachings. It is therefore to be understood that, within the scope of the appended claims, the invention may be practiced otherwise than as specifically described.

What is claimed:

1. A method comprising:

a) illuminating a sample with substantially monochromatic light, b) illuminating the sample with broad band light;

c) collecting a spectrum of Raman scattered light from the sample;

d) collecting a spectrum of light transmitted through the sample in a near infrared spectral range;

e) forming a first spatially accurate wavelength resolved image of the sample using Raman scattered light and a second spatially accurate wavelength resolved image using light transmitted through the sample;

f) analyzing the first spatially accurate wavelength resolved image and the second spatially accurate wavelength resolved image for patterns characteristic of a pathogenic microorganism; and (g) based on said analyzing, identifying the pathogenic microorganism.

2. The method of claim 1 further comprising passing the Raman scattered light from the sample and light transmitted through the sample through a filter selected from the group consisting of a tunable filter, a band pass filter, a liquid crystal tunable filter, an interferometer, an acousto optic tunable filter, a dispersive optical device and a computed tomography imaging spectrometer.

3. The method of claim 1 further comprising providing spatially resolved Raman spectra.

4. The method of claim 1 further comprising providing spatially resolved near infrared spectra.

5. The method of claim 1 further comprising analyzing the patterns characteristic of the pathogenic microorganism to determine viability of the pathogenic microorganism.

6. The method of claim 1 further comprising analyzing the patterns characteristic of the pathogenic microorganism to determine a growth medium in which the pathogenic microorganism was grown.

7. The method of claim 1 further comprising analyzing the patterns characteristic of the pathogenic microorganism to determine a strain of the pathogenic microorganism.

8. The method of claim 1 further comprising analyzing the first spatially accurate wavelength resolved image and the second spatially accurate wavelength resolved image for patterns characteristic of one of a biological material and a non-biological material.

9. The method of claim 1 wherein the pathogenic microorganism is selected from the group of viruses consisting of filoviruses, naviruses, and alphaviruses.

10. The method of claim 1 wherein the pathogenic microorganism is selected from the group of microorganisms consisting of protozoa, cryptosporidia microorganisms, *Escherichia coli, Escherichia coli* 157 microorganisms, Plague (*Yersinia pestis*), Smallpox (*variola major*), Tularemia (*Francisella tularensis*), Brucellosis (*Brucella* species), *Clostridium perfringens, Salmonella, Shigella,* Glanders (*Burkholderia mallei*), Melioidosis (*Burkholderia pseudomallei*), Psittacosis (*Chlamydia psittaci*), Q fever (*Coxiella burnetil*), Typhus fever (*Rickettsia prowazekii*), and *Vibrio cholerae.*

11. The method of claim 1 wherein the pathogenic microorganism is selected from the group of bacteria consisting of *Giardia, Candida albicans, Enterococcus faecalis, Staphylococcus epidermidis, Staphylococcus aureus, Enterobacter aerogenes, Corynebacterium diphtheriae, Pseudomonas eruginosa, Acinetobacter calcoaceticus, Klebsiella pneumoniae*, and *Serratia marcescens.*

12. The method of claim 1 wherein in the pathogenic microorganism is selected from the group of fungus consisting of *Microsporum audouini, Microspotum canis, Microsporum gypseum, Trichophyton mentagrophytes* var. *mentagrophytes, Trichophyton mentagrophytes* var. *interdigitale, Trichophyton rubrum, Trichophyton tonsurans, Trichophyton verrucosum*, and *Epidermophytum floccosum.*

13. A method comprising:
a) illuminating a sample with substantially monochromatic light,
b) illuminating the sample with broad band light;
c) passing the Raman scattered light and light transmitted through the sample through a FAST fiber array spectral translator;
d) collecting a spectrum of Raman scattered light from the sample;
e) collecting a spectrum of light transmitted through the sample in a near infrared spectral range;
f) forming a first spatially accurate wavelength resolved image of the sample using Raman scattered light and a second spatially accurate wavelength resolved image using light transmitted through the sample;
g) analyzing the first spatially accurate wavelength resolved image and the second spatially accurate wavelength resolved image for patterns characteristic of a pathogenic microorganism; and
(h) based on said analyzing, identifying the pathogenic microorganism.

14. The method of claim 13 further comprising passing the Raman scattered light and light transmitted through the sample through a filter selected from the group consisting of a tunable filter, a band pass filter, a liquid crystal tunable filter, an interferometer, an acousto optic tunable filter, a dispersive optical device and a computed tomography imaging spectrometer.

15. The method of claim 13 further comprising providing spatially resolved Raman spectra.

16. The method of claim 13 further comprising providing spatially resolved near infrared spectra.

17. The method of claim 13 further comprising analyzing the patterns characteristic of the pathogenic microorganism to determine viability of the pathogenic microorganism.

18. The method of claim 13 further comprising analyzing the patterns characteristic of the pathogenic microorganism to determine a growth medium in which the pathogenic microorganism was grown.

19. The method of claim 13 further comprising analyzing the patterns characteristic of the pathogenic microorganism to determine a strain of the pathogenic microorganism.

20. The method of claim 13 further comprising analyzing the first spatially accurate wavelength resolved image and the second spatially accurate wavelength resolved image for patterns characteristic of one of a biological material and a non-biological material.

21. The method of claim 13 wherein the pathogenic microorganism is selected from the group of viruses consisting of filoviruses, naviruses, and alphaviruses.

22. The method of claim 13 wherein the pathogenic microorganism is selected from the group of microorganisms consisting of protozoa, cryptosporidia microorganisms, *Escherichia coli*, *Escherichia coli* 157 microorganisms, Plague (*Yersinia pestis*), Smallpox (*variola major*), Tularemia (*Francisella tularensis*), Brucellosis (*Brucella* species), *Clostridium perfringens*, *Salmonella*, *Shigella*, Glanders (*Burkholderia mallei*), Melioidosis (*Burkholderia pseudomallei*), Psittacosis (*Chlamydia psittaci*), Q fever (*Coxiella burnetil*), Typhus fever (*Rickettsia prowazekii*), and *Vibrio cholerae*.

23. The method of claim 13 wherein the pathogenic microorganism is selected from the group of bacteria consisting of *Giardia*, *Candida albicans*, *Enterococcus faecalis*, *Staphylococcus epidermidis*, *Staphylococcus aureus*, *Enterobacter aerogenes*, *Corynebacterium diphtheriae*, *Pseudomonas eruginosa*, *Acinetobacter calcoaceticus*, *Klebsiella pneumoniae*, and *Serratia marcescens*.

24. The method of claim 13 wherein in the pathogenic microorganism is selected from the group of fungus consisting of *Microsporum audouini*, *Microspotum canis*, *Microsporum gypseum*, *Trichophyton mentagrophytes* var. *mentagrophytes*, *Trichophyton mentagrophytes* var. *interdigitale*, *Trichophyton rubrum*, *Trichophyton tonsurans*, *Trichophyton verrucosum*, and *Epidermophytum floccosum*.

* * * * *